US00RE46372E

(19) United States
(12) Reissued Patent
Miller et al.

(10) Patent Number: US RE46,372 E
(45) Date of Reissued Patent: Apr. 25, 2017

(54) METHOD FOR TREATING HEARING LOSS

(71) Applicant: The Regents of the University of Michigan, Ann Arbor, MI (US)

(72) Inventors: Josef M. Miller, Ann Arbor, MI (US); Glenn E. Green, Dexter, MI (US); Colleen G. LePrell, Gainesville, FL (US)

(73) Assignee: THE REGENTS OF THE UNIVERITY OF MICHIGAN, Ann Arbor, MI (US)

(21) Appl. No.: 15/089,849

(22) Filed: Apr. 4, 2016

Related U.S. Patent Documents

Reissue of:
(64) Patent No.: 9,144,565
Issued: Sep. 29, 2015
Appl. No.: 13/839,760
Filed: Mar. 15, 2013

U.S. Applications:
(63) Continuation-in-part of application No. 13/679,224, filed on Nov. 16, 2012, now Pat. No. 8,927,528, which is a continuation-in-part of application No. 12/761,121, filed on Apr. 15, 2010, now Pat. No. 8,338,397, which is a continuation-in-part of application No. 11/623,888, filed on Jan. 17, 2007, now Pat. No. 7,951,845, said application No. 13/679,224 is a continuation-in-part of application No. 13/091,931, filed on Apr. 21, 2011, now Pat. No. 8,338,398, which is a continuation of application No. 11/623,888, filed on Jan. 17, 2007, now Pat. No. 7,951,845.

(60) Provisional application No. 60/760,055, filed on Jan. 19, 2006.

(51) Int. Cl.

| | |
|---|---|
| ***A61K 33/06*** | (2006.01) |
| ***A61K 31/60*** | (2006.01) |
| ***A61K 31/355*** | (2006.01) |
| ***A61K 31/341*** | (2006.01) |
| ***A61K 31/05*** | (2006.01) |
| ***A61K 45/06*** | (2006.01) |
| ***A61K 31/07*** | (2006.01) |
| ***A61K 31/245*** | (2006.01) |
| ***A61K 33/00*** | (2006.01) |
| ***A61K 31/375*** | (2006.01) |

(52) U.S. Cl.
CPC ..... *A61K 31/355* (2013.01); *A61K 31/05* (2013.01); *A61K 31/07* (2013.01); *A61K 31/341* (2013.01); *A61K 31/375* (2013.01); *A61K 33/00* (2013.01); *A61K 33/06* (2013.01); *A61K 45/06* (2013.01)

(58) Field of Classification Search
CPC ..... A61K 33/06; A61K 31/60; A61K 31/355; A61K 31/341; A61K 31/05; A61K 45/06; A61K 31/07; A61K 31/245; A61K 33/00; A61K 31/375
See application file for complete search history.

(56) References Cited

U.S. PATENT DOCUMENTS

| | | | |
|---|---|---|---|
| 5,597,585 | A | 1/1997 | Williams et al. |
| 6,093,417 | A | 7/2000 | Petrus |
| 6,177,434 | B1 | 1/2001 | Kopke et al. |
| 6,265,386 | B1 | 7/2001 | Campbell |
| 6,288,106 | B1 | 9/2001 | Pearson et al. |
| 6,423,321 | B2 | 7/2002 | Tobinick |
| 6,524,619 | B2 | 2/2003 | Pearson et al. |
| 6,562,378 | B1 | 5/2003 | Chandra |
| 6,649,621 | B2 | 11/2003 | Kopke et al. |
| 6,660,297 | B2 | 12/2003 | Bartels et al. |
| 6,815,434 | B2 | 11/2004 | Kil et al. |
| 7,786,100 | B2 | 8/2010 | Miller et al. |
| 7,951,845 | B2 | 5/2011 | Miller et al. |
| 8,053,424 | B2 | 11/2011 | Miller et al. |
| 8,338,397 | B2 | 12/2012 | Miller |
| 8,338,398 | B2 | 12/2012 | Miller et al. |
| 2002/0061870 | A1 | 5/2002 | Pearson et al. |
| 2003/0191064 | A1 | 10/2003 | Kopke |
| 2004/0033273 | A1 | 2/2004 | Patwardhan et al. |
| 2004/0096524 | A1 | 5/2004 | Nair et al. |
| 2004/0101560 | A1 | 5/2004 | Sawchuk et al. |
| 2004/0224012 | A1 | 11/2004 | Suvanprakorn et al. |
| 2004/0247570 | A1 | 12/2004 | Miller et al. |
| 2004/0258781 | A1 | 12/2004 | Nair et al. |
| 2005/0013854 | A1 | 1/2005 | Mannino et al. |
| 2005/0070607 | A1 | 3/2005 | Andrus et al. |

(Continued)

FOREIGN PATENT DOCUMENTS

| | | |
|---|---|---|
| EP | 1 258 243 A1 | 11/2002 |
| EP | 1258243 | 11/2002 |
| WO | WO 98/56761 | 12/1998 |

(Continued)

OTHER PUBLICATIONS

Colleen G. Le Prell et al. "Free radical scavengers vitamins A, C, and E plus magnesium reduce noise trauma," Free Radical Biology & Medicine. (2007) 42:1454-1463.*

Ohinata, "Intense noise induces formation of vasoactive lipid peroxidation products in the cochlea", Brain Res. 878, 2000, pp. 163-173.

Ohinata et al., "Protection from noise-induced lipid peroxidation and hair cell loss in the cochlea", Brain Res. 966, 2003, pp. 265-273.

Ohlemiller et al., "Early Elevation of Cochlear Reactive Oxygen Species following Noise Exposure", Audiol Neurootol 4, 1999, pp. 229-236.

Oleinick et al., "The Photobiology of Photodynamic Therapy: Cellular Targets and Mechanisms", Radiation Research 150 (Suppl.), 1998, pp. S146-S156.

(Continued)

*Primary Examiner* — Johnny F Railey
(74) *Attorney, Agent, or Firm* — Howard & Howard Attorneys PLLC

(57) ABSTRACT

A method of treating hearing loss includes the step administering a composition to the mammal, wherein the composition consists essentially of a biologically effective amount of vitamin A, vitamin E, vitamin C, a vasodilator comprising magnesium, and, optionally, a withanolide, and/or resveratrol.

24 Claims, 22 Drawing Sheets

(56) References Cited

U.S. PATENT DOCUMENTS

| | | | |
|---|---|---|---|
| 2005/0107338 | A1 | 5/2005 | Seidman |
| 2015/0374659 | A1 | 12/2015 | Miller et al. |

FOREIGN PATENT DOCUMENTS

| | | | |
|---|---|---|---|
| WO | WO 98/56761 | A2 | 12/1998 |
| WO | WO 01/84961 | | 5/2001 |
| WO | WO 01/84961 | A2 | 11/2001 |
| WO | WO 03/030818 | | 4/2003 |
| WO | WO 03/030818 | A2 | 4/2003 |
| WO | WO 2004/000297 | | 12/2003 |
| WO | WO 2004/000297 | A1 | 12/2003 |
| WO | WO 2004/016100 | | 2/2004 |
| WO | WO 2004/016100 | A2 | 2/2004 |
| WO | WO 2004/037205 | | 5/2004 |
| WO | WO 2004/037205 | A2 | 5/2004 |
| WO | WO 2004/050021 | | 6/2004 |
| WO | WO 2004/050021 | A2 | 6/2004 |

OTHER PUBLICATIONS

Omenn et al., "Effects of a combination of beta carotene and vitamin A on lung cancer and cardiovascular disease", N. Engl. J. Med. 334, 1996, pp. 1150-1155.
Perlman et al., "Cochlear blood flow and acoustic trauma", Acta Otolaryngol. (Stockh). 54, 1962, pp. 99-119.
Pierson et al., "Prophylaxis of kanamycin-induced ototoxicity by a radioprotectant", Hear Res 4, 1981, pp. 79-87.
Priuska et al., "Formation of free radicals by gentamicin and iron and evidence for an iron-gentamicin complex", Biochem Pharmacol 50(11), 1995, pp. 1749-1752.
Rabinowitz et al., "Antioxidant status and hearing function in noise-exposed workers", Hear. Res. 173, 2002, pp. 164-171.
Romeo, "The Therapeutic Effect of Vitamins A and E in Neurosensory Hearing Loss", [Italian] Journal Article—Acta Vitamminol. Enzymol. 7 Suppl, 1985, pp. 85-92, 1 Page English Abstract from OVID Search Results.
Rybak et al., "Ototoxicity", Kidney International 72, 2007, pp. 931-935.
Schact, "Antioxidant therapy attenuates aminoglycoside-induced hearing loss", Ann. N. Y. Acad. Sci. 884, 1999, pp. 125-130.
Scheibe et al. "Preventive effect of magnesium supplement on noise-induced hearing loss in the guinea pig", Eur. Arch. Otorhinolaryngol. 257, 2000, pp. 10-16.
Scheibe et al., "Preventive magnesium supplement reduces ischemia-induced hearing loss and blood viscosity in the guinea pig", Eur Arch Otorhinolaryngol 257, 2000, pp. 355-361.
Scheibe et al. "Therapeutic effect of parenteral magnesium on noise-induced hearing loss in the guinea pig", Magnes. Res. 15, 2002, pp. 27-36.
Scheibe et al., "Total magnesium concentrations of perilymph, cerebrospinal fluid and blood in guinea pigs fed different magnesium-containing diets", Eur. Arch. Otorhinolaryngol. 256, 1999, pp. 215-219.
Schneider et al., "Gingko biloba (Rokan) therapy in tinnitus patients and measurable interactions between tinnitus 3nd vestibular disturbances", Int. Tinnitus J. 6, 2000, pp. 56-62.
Seidman, "Effects of dietary restriction and antioxidants on presbyacusis", Laryngoscope 110, 2000, pp. 27-38.
Seidman et al., "Effects of resveratrol on acoustic trauma", Otolaryngol. Head Neck Surg. 129, 2002, pp. 463-470.
Sergi et al., "The role of antioxidants in protection from ototoxic drugs", Acta Otolaryngol. Suppl. (Stockh), 2004, pp. 42-45.
Sha et al., "Aspirin to prevent gentamicin-induced hearing loss", N Engl J Med 354(17), 2006, pp. 1856-1857.
Sha et al., "Formation of reactive oxygen species following bioactivation of gentamicin", Free Rad Biol Med 26(3-4), 1999, pp. 341-347.
Sha et al., "Salicylate attenuates gentamicin-induced ototoxicity", Lab Invest 79, pp. 807-813.
Song et al.,"Iron chelators protect from aminoglycosideinduced cochleo- and vestibulotoxicity in guinea pig", Free Radic. Biol. Med. 25, 1998, pp. 189-195.
Song et al., "Variable efficacy of radical scavengers and iron chelators to attenuate gentamicin ototoxicity in guinea in pig in vivo", Hear Res 94, 1996, pp. 87-93.
Soares et al., "Sequestering Ability of Butylated Hydroxytoluene, Propyl Gallate, Resveratrol, and Vitamins C and E against ABTS, DPPH, and Hydroxul Free Radicals in Chemical and Biological Systems", J. Agric. Food Chem. 51, 2003, pp. 1077-1080.
Takumida et al., "Radical scavengers for Meniere's disease after failure of conventional therapy: a pilot study", Acta Otolaryngol. (Stockh). 123, 2003, pp. 697-703.
Tanswell et al., "Antioxidant therapy in critical care medicine", New Horizons 3, 1995, pp. 330-341, 1 page abstract from OVID:Search Results on Apr. 22, 2006.
Teranishi et al., "Effects of alpha-tocopherol on cisplatin-induced ototoxicity in guinea pigs", Hear. Res. 151, 2011, pp. 61-70.
Usami et al., "Differential cellular distribution of glutathione—an endogenous antioxidant—in the guinea pig inner ear", Brain Res. 743, 1996, pp. 337-340.
Wang et al., "Bcl-XL disrupts death-inducing signal complex formation in plasma membrane induced by hypoxia/reoxygenation", The FASEB Journal, Research Communication, pp. 1826-1833.
Wangemann, "K+ Cycling and Its Regulation in the Cochlea and the Vestibular Labyrinth", Audiol Neurootol 7, 2002, pp. 199-205.
Wangemann, "K+ Cycling and the endocochlear potential", Hearing Research 165, 2002, pp. 1-9.
Watanabe et al., "Acoustic stimulation promotes the expression of inducible nitric oxide synthase in the vestibule of guinea pigs", Acta Otolaryngol. Suppl. 553: (Stockh)., 2004, pp. 54-57.
Weijl et al., "Supplementation with antioxidant micronutrients and chemotherapy-induced toxicity in cancer patients treated with cisplatin-based chemotherapy: a randomised, double-blind, placebo-controlled study", Eur. J. Cancer 40, 2004, pp. 1713-1723.
Yamashita et al., "Post-exposure treatment attenuates noise-induced hearing loss", Neuroscience, 134, 2005, pp. 633-642.
Yamashita, et al., "Delayed production of free radicals following noise exposure", Brain Res 1019, 2004, pp. 201-209.
Agrawal, Y., et al., "Prevalence of Hearing Loss and Differences by Demographic Characteristics Among U.S. Adults", Data from the National Health and Nutrition Examination Survey, 1999-2004. Arch Intern Med. 2008; 168, pp. 1522-1530.
Labdiet, "PicoLab Laboratory Rodent Diet", Jan. 9, 2014, 1 page.
Population Reference Bureau, "Human Population: Urbanization, Largest Urban Agglomerations, 1975, 2000, 2025, Teachers Guide: Discussion Guide", originally downloaded from http://www.prb.org/Publications/Less-Plans/HumanPopulation/Urbanization.aspx on Aug. 27, 2016.
World Health Organization, "Hearing Loss Due to Recreational Exposure to Loud Sounds: A Review", 2015, pp. 1-32.
World Health Organization, "Who Global Estimates on Prevalence of Hearing Loss—Mortality and Burden of Diseases and Prevention of Blindness and Deafness", 2012, 15 pages.
Yamasoba, T., "Oxidative Stress in Applied Basic Research and Clinical Practice, Oxidative Stress and Age-Related Hearing Loss, Part VI—Interventions to Prevent Age-Related Hearing Loss", Free Radicals in ENT Pathology, Eds.: Miller, J., Le Press, C and Rybak, L., Humana Press, 2015, pp. 335-349.
Utility U.S. Appl. No. 15/272,973, filed Sep. 22, 2016.
Utility U.S. Appl. No. 15/272,981, filed Sep. 22, 2016.
Altura et al., Role of Mg ions in contractility of blood vessels and skeletal muscles. Magnesium-B 1a, 1981, pp. 102-114.
Aoshiba et al., "Acute cigarette smoke exposure induces apoptosis of alveolar macrophages", Am J Physiol Lung Cell Mol Physiol 281, 2001, pp. L1392-L1401.
Attias et al, Oral magnesium intake reduces permanent hearing loss induced by noise exposure. Am. J. Otolaryngol. 15, 2004, pp. 26-32.
Attias et al.,"Preventing noise induced otoacoustic emission loss by increasing magnesium (Mg2+) intake in guinea-pigs." J. Basic Clin. Physiol. Pharmacol. 14, 2003, pp. 119-136.
Balavoine et al., "Peroxynitrite scavenging by different antioxidants. Part I: Convenient Assay", Nitric Oxide 3, 1999, pp. 40-54.

(56) References Cited

OTHER PUBLICATIONS

Bertolaso et al., "Apoptosis in the OC-k3 immortalized cell line treated with different agents", Audiology 40, 2001, pp. 327-335.
Biesalski, et al., "Vitamin A deficiency increases noise susceptibility in guinea pigs", J. Nutr. 120, 1990, pp. 726-737.
Bock et al., "Effects of N-acetylcysteine on kanamycin ototoxicity in the guinea pig", Hear Res 9, 1983, pp. 255-262.
Boland et al., "Pre- and post-treatment with pirlindole and dehydropirlindole protects cultured brain cells against nitric oxide-induced death", Eur J Pharmacol 466, 2003, pp. 21-30.
Cevette et al., "Magnesium and hearing", J. Am. Acad. Audiol. 14, 2003, pp. 202-212.
Chae et al., "Salicylate regulates COX-2 expression through ERK and subsequent NF-kappaB activation in osteoblasts", Immunopharmacol Immunotoxicol 26, 2004, pp. 75-91.
Chan et al., "Connexin-26-associated deafness: phenotypic variability and progression of hearing loss", Genet Med. 2010,12, pp. 174-181.
Cryns et al., "A genotype-phenotype correlation for GJB2 (connexin 26) deafness", J Med Genet 2004, 41, pp. 147-154.
Diamond et al., Ginkgo biloba extract: mechanisms and clinical indications. Arch. Phys. Med. Rehabil. 81, 2000, pp. 668-678.
Didier et al., "Effects of Ginkgo biloba extract (EGb 761) on cochlear vasculature in the guinea pig: morphometric measurements and laser Doppler flowmetry", Eur. Arch. Otorhinolaryngol. 253, 1996, pp. 25-30.
Duan et al., "Dose and time-dependent protection of the antioxidant N-L-acetylcysteine against impulse noise trauma", Hear. Res. 192, 2004 pp. 1-9.
Eliseev et al., "Bcl-2 and tBid proteins counter-regulate mitochondrial potassium transport", Biochimica et Biophysica Acta 1604, 2003, pp. 1-5.
Evans et al., "Free radicals and hearing. Cause, consequence, and criteria", Ann. N. Y. Acad. Sci. 884, 1999, pp. 19-40.
Fetoni et al., Alpha-Tocopherol protective effects on gentamicin ototoxicity: an experimental study. Int J Audiol 43, 2004, pp. 166-171.
Floyd, "Antioxidants, oxidative stress, and degenerative neurological disorders", Proc Soc Exp Biol Med 222, 1999, pp. 236-245.
Forge et al., "Aminoglycoside Antibiotics", Audiol Neurootol 5, 2000, pp. 3-22.
Garetz et al., "Sulphydryl compounds and antioxidants inhibit cytotoxicity to outer hair cells of a gentamicin metabolite in vitro", Hear Res 77, 1994, pp. 75-80.
Godar, "UVA1 Radiation Triggers Two Different Final Apoptotic Pathways", The Society for Investigative Dermatology Inc., 1999, pp. 3-12.
Gordin et al., Magnesium: a new therapy for idiopathic sudden sensorineural hearing loss. Otol. Neurotol. 23, 2002, pp. 447-451.
Green et al., "Audiological Manifestations and Features of Connexin 26 Deafness", Aud Med. 2003,1, pp. 5-11.
Green et al., "Genetic testing to identify deaf newborns", JAMA. 284, 2000, p. 1245.
Green et al., "Presentation, Hearing Improvement on A CEMg in a Child with Connexin 26 Hearing Loss", Feb. 2011 (University of Michigan, University of Florida), 5 pages.
Gunther et al., "Biochemical mechanisms affecting susceptibility to noise-induced hearing loss", Am. J. Otol. 10, 1989, pp. 36-41.
Gutteridge et al., "Antioxidant protection and oxygen radical signaling. In: Gilbert, D.L., Colton, CA., (Eds.), Reactive oxygen species in biological systems: An interdisciplinary approach", Kluwer Academic/Plenum Publishers, New York. 1999, pp. 189-218.
Halliwell, "Free Radicals In Biology and Medicine", 3rd Ed., Oxford Univ. Press (1999), Chapter 3—Antioxidant defences, pp. 105-245.
Haupt et al., Preventive magnesium supplement protects the inner ear against noise-induced impairment of blood flow and oxygenation in the guinea pig. Magnes. Res. 15, 2002, pp. 17-25.
Haupt et al., "Therapeutic efficacy of magnesium in acoustic trauma in the guinea pig", ORL. J. Otorhinolaryngol. Relat. Spec. 65, 2003, pp. 134-139.
Henderson et al., The role of antioxidants in protection from impulse noise. Ann. N. Y. Acad. Sci. 884, 1999, pp. 368-380.
Hight et al., "Noise-induced hearing loss in chinchillas pre-treated with glutathione monoethylester and R-PIA", Hear. Res. 179, 2003, pp. 21-32.
Hilgert et al., "Forty-six genes causing nonsyndomic hearing impairment: Which ones should be analyzed in DNA diagnostics?", Mutation Research 681, 2009, pp. 189-196.
Hoffman et al., "Potentiation of ototoxicity by glutathione depletion", Ann Ototol Rhinol Laryngol 97, 1, 1988, pp. 36-41.
Hou et al., "Effects of alpha-tocopherol on noise-induced hearing loss in guinea pigs", Hear. Res. 179, 2003, pp. 1-8.
Hu et al., "R-phenylisopropyladenosine attenuates noise-induced hearing loss in the chinchilla". Hear. Res. 113, 1997, pp. 198-206.
Inoue et al., "ATP-sensitive K+ channel in the mitochondrial inner membrane", Letters to Nature, vol. 352, Jul. 18, 1991, pp. 244-247.
Ising et al., "Increased noise trauma in guinea pigs through magnesium deficiency", Arch. Otorhinolaryngol. 236, 1982, pp. 139-146.
Jackson et al., "Antioxidant strategies for post-noise hearing loss recovery, International Symposium—Pharmacologic Strategies for Prevention and Treatment of Hearing Loss and Tinnitus", Niagra Falls, Ottawa, Canada, 2005, 1 page.
Jacono et al., "Changes in cochlear antioxidant enzyme activity after sound conditioning and noise exposure in the chinchilla", Hear Res 117, 1998, pp. 31-38.
Joachims et al., "Antioxidants in treatment of idiopathic sudden hearing loss", Otol. Neurotol. 24, 2003, pp. 572-575.
Joachims et al., (1983). Dependence of noise-induced hearing loss upon perilymph magnesium concentration, J. Acoust. Soc. Am. 74, 1983, pp. 104-108.
Joachims et al., "Oral magnesium supplementation as prophylaxis for noise-induced hearing loss: results of a double blind field study", Schrittenr. Ver. Wasser. Boden. Lufthyg. 88, 1993, pp. 511-516.
Jung et al., "Effects of Ginkgo biloba extract on the cochlear damage induced by local gentamicin installation in guinea pigs", J. Korean Med. Sci. 13, 1998, pp. 525-528.
Kalkanis et al., "Vitamin E reduces cisplatin ototoxicity", Laryngoscope 114, 2004, pp. 538-542.
Kenna et al., "Audiologic phenotype and progression in GJB2 (Connexin 26) hearing loss", Arch Otolaryngol Head Neck Surg. 36(1), 2010, pp. 81-87.
Knight, "Popping pill may prevent hearing loss", [Online] http://www.newscientist.com/article.ns?id=dn2666 (posted Aug. 13, 2002; verified Feb. 25, 2005), 2 pages.
Kopke et al., "A radical demise-Toxins and trauma share common pathways in hair cell death", Ann N Y Acad Sci 884, 1999, pp. 171-191.
Kopke et al., "Candidate's thesis: Enhancing intrinsic cochlear stress defenses to reduce noise-induced hearing loss", Laryngoscope 112, 2002, pp. 1515-1532.
Kopke, "NAC for Noise: From the bench top to the clinic," International Symposium—Pharmacologic Strategies for Prevention and Treatment of Hearing Loss and Tinnitus, Niagra Falls, Ottawa, Canada, 2005, 1 page.
Kopke et al., "Reduction of noise-induced hearing loss using L-NAC and salicylate in the chinchilla", Hear. Res. 149, 2000, pp. 138-146.
Kujawa et al., "Acceleration of Age-Related Hearing Loss by Early Noise Exposure: Evidence of a Misspent Youth," Journal of Neuro., Feb. 15, 2006, 26(7), pp. 2115-2123.
Kujawa, "Adding insult to injury: Noise-induced and age-related hearing loss interactions," International Symposium—Pharmacologic Strategies for Prevention and Treatment of Hearing Loss and Tinnitus, Niagra Falls, Ottawa, Canada, 2005, 1 page.
Kwon et al., "Sodium salicylate inhibits expression of COX-2 through suppression of ERK and subsequent NF-cappaB activation in rat ventricular cardiomyocytes", Arch Pharm Res 26, 2003, pp. 545-553.

(56) References Cited

OTHER PUBLICATIONS

Lautermann et al., "Glutathione protection against gentamicin ototoxicity depends on nutritional status", Hear Res 86, 1995, pp. 15-24.
Le Prell et al., Pathways for protection from noise induced hearing loss, Noise Health 5, 2003, pp. 1-17.
Li et al., "Salicylate protects hearing and kidney function from cisplatin toxicity without compromising its oncolytic action",Lab Invest 82, 2002, pp. 585-596.
Lohle, "The influence of a chronic vitamin A deficiency on the acoustic sensory cells and the ganglion spirale cochleae of the rat", An electron microscope study. Arch. Otorhinolaryngol. 229, 1980, pp. 45-53.
Lohle, "Ultrastructural changes in the organ of Corti and in the ganglion spiral cochleae after vitamin A deficiency", Pathol. Res. Pract. 179, 1985, pp. 560-567.
Lopez-Gonzalez et al., "Ototoxicity caused by cisplatin is ameliorated by melatonin and other antioxidants", J. Pineal Res. 28, 2000, pp. 73-80.
Martinez et al., "Gap-Junction Channel Dysfunction in Deafness and Hearing Loss," Antioxidants & Redox Signaling, vol. 11, No. 2, 2009, pp. 309-372.
McFadden et al., "Dietary Vitamin C Supplementation Reduces Noise-Induced Hearing Loss In Guinea Pigs", Hearing Research 202, 2005, pp. 200-208.
Miller et al., "Mechanisms and Prevention of Noise-Induced Hearling Loss", Otol Jpn, 16(2), 2006, p. 139.
Miller et al., "8-iso-prostaglandin F(2alpha), a product of noise exposure, reduces inner ear blood flow", Audiol. Neurootol. 8, 2003, pp. 207-221.
Morton et al., "Newborn Hearing Screening—A Silent Revolution", New Engl J Med 354, 2006, pp. 2151-2164.
Nageris et al., "Magnesium treatment for sudden hearing loss", Ann. Otol. Rhinol. Laryngol. 113, 2004, pp. 372-675.
Nickel et al., "Gap junctions and connexins in the inner ear: their roles in homeostasis and deafness", Current opinion in Otolryngology & head and Neck Surgery 16, 2008, pp. 452-457.
Niki, "Action of ascorbic acid as a scavenger of active and stable oxygen radicals", Am J Clin Nutr 54, 1991, pp. 1119S-1124S.
Niki et al., "Interation among Vitamin C, Vitamin E, and Beta-Carotene 1-3", Am J Clin Nutr 62(suppl), 1995, pp. 1322S-1326S.
Niki, "Interaction of Ascorbate and Alpha-Tocophpperol", Department of Reaction Chemistry, Faculty of Engineering, University of Tokyo, pp. 186-199.
Yamasoba et al., "Role of glutathione in protection against noise-induced hearing loss", Brain Res. 784, 1998, pp. 82-90.
Yamasoba et al., "Influence of intense sound exposure on glutathione synthesis in the cochlea", Brain Research 804, 1998, pp. 72-78.
The Alpha-Tocopherol, Beta Carotene Cancer Prevention Study Group. The effect of vitamin E and beta carotene on be incidence of lung cancer and other cancers in male smokers. N. Engl. J. Med. 330, 1994, pp. 1029-1035.
Constricted Blood Vessels, downloaded from http://www.menieres.org/forums/NonCGI/Forum1/HTML/003686.html, 1 page.
"A Randomized, Placebo-Controlled, Clinical Trial of High-Dose Supplementation With Vitamins C and E, Beta Carotene and Zinc for Age-Related Degeneration and Vision Loss", Arch Ophthalmol, 119(10), Oct. 2001, pp. 1417-1436.
Cohen-Salmon et al., "Targeting Ablation of Connexin26 in the Inner Ear Epithelial Gap Junction Network Causes Hearing Impairment and Cell Death", Current Biology, vol. 12, Jul. 9, 2002, pp. 1106-1111.
Green GE, Mueller RF, Cohn ES, Avraham KB, Kanaan M, Smith RJH. Audiological Manifestations and Features of Connexin 26 Deafness. Aud Med. 2003;1:5-11.
Ahn et al., Anti-Apoptotic Role of Retinoic Acid in the Inner Ear of Noise-Exposed Mice, Biochemical and Biophysical Research Communications 335, 2005, pp. 485-490.
Abaamrane et al., "Long-term Administration of Magnesium After Acoustic Trauma Caused by Gunshot Noise in Guinea Pigs", Hearing Research 247, 2009, pp. 137-145.
Attias et al., "Reduction in Noise-Induced Temporary Threshold Shift in Humans Following Oral Magnesium Intake", Clinical Otolaryngology 29, Blackwell Publishing Ltd, 2004, pp. 635-641.
Branis et al., "Effect of Ascorbic Acid on the Numerical Hair Cell Loss in Noise Exposed Guinea Pigs", Hearing Research 33, Elsevier Science Publishers B.V., 1988, pp. 137-140.
Fischer et al., "Protection of the Cochlea by Ascorbic Acid in Noise Trauma", HNO 57(4) , Apr. 2009, pp. 339-344.
English language abstract for Fischer et al., "Protection of the Cochlea by Ascorbic Acid in Noise Trauma", HNO 57 (4) , Apr. 2009, pp. 339-344.
Heinrich et al, "Ascorbic Acid Reduces Noise-Induced Nitric Oxide Production in the Guinea Pig Ear", Laryngoscope 118, The American Laryngological, Rhinological and Otological Society, Inc., May 2008, pp. 837-842.
Laurikainen et al., "Betahistine Effects on Cochlear Blood Flow: From the Laboratory to the Clinic", Acta Otolaryngol, Supp. 544, 2000, pp. 5-7.
Laurikainen et al., "Non-Specific Effect of Beettahistine on Cochlear Electrophysiology in Guinea Pig", Acta Otolayngol (Stockh), Supp. 529, 1997, pp. 77-79.
Le Prell et al., "Free Radical Scavengers Vitamins A, C and E Plus Magnesium Reduce Noise Trauma", Free Radical Biology & Medicine 42, 2007, pp. 1454-1463.
Le Prell et al., "Mechanisms of Noise-Induced Hearing Loss Indicate Multiple Methods of Prevention", Hearing Research 226, Elsevier B.V., 2007, pp. 22-43.
McFadden, S.L., Wo, J.M., Michalak, N. Ding D., Dietary Vitamin C Supplementation Reduces Noise-Induced Hearing Loss in Guinea Pigs, Hearing Research 202 (2005) 200-208.
Miller et al., "Interactive Effects of Aging with Noise Induced Hearing Loss", Scand. Audiol, 27, 1998, pp. 53-61.
Minami et al., "Creatine and Tempol Attenuate Noise-Induced Hearing Loss", Brain Res. May 7, 2007, pp. 1-13.
Ohinata, Y., Yamasoba, T., Schacht, J., Miller, J. M. (2000b). Glutathione limits noise-induced hearing loss. Hear. Res. 146, 28-34.
Shoji et al., "Differential Protective Effects of Neurotrophins in the Attenuation of Noise-Induced Hair Cell Loss", Hearing Research 146, 2000, pp. 134-142.
Takemura et al., "Direct Inner Ear Infusion of Dexamethasone Attenuates Noise-Induced Trauma in Guinea Pig", Hearing Research 196, 2004, pp. 58-68.
Yamasoba et al., "Attenuation of Cochlear Damage From Noise Trauma by an Iron Chelator, a Free Radical Scavenger and Glial Cell Line-Derived Neurotrophic Factor in Vivo", Brain Research 815, 1999, pp. 317-325.
http://www.menieres.org/forums/NonCGI/Forum1/HTML/003686.html Constricted Blood Vessels, 1 Page, 2005.
International Search Report, International Application No. PCT/US07/01422, Mar. 4, 2008, 2 pages.
K. Cryns et al., "A genotype-phenotype correlation for GJB2 (connexin 26) deafness", J Med Genet 2004; 41: 147-154.
Szabo et al., "A Novel Potassium Channel in Lymphocyte Mitochondria", The Journal of Biological Chemistry, vol. 280, No. 13, Apr. 1, 2005, pp. 12790-12798.
Etsuo Niki, "Action of ascorbic acid as a scavenger of active and stable oxygen radicals", Am J Clin Nutr 1991; 54: 1119S-24S.
Tsuchihashi et al., "Action of Beta-Carotene as an Antioxidant against Lipid Peroxidation", Archives of Biochemistry and Biophysics, vol. 323, No. 1, Oct. 20, 1995, pp. 137-147.
Aoshiba et al., "Acute cigarette smoke exposure induces apoptosis of alveolar macrophages", Am J Physiol Lung Cell Mol Physiol 281: L1392-L1401, 2001.
"A Randomized, Placebo-Controlled, Clinical Trial of High-Dose Supplementation With Vitamins C and E, Beta Carotene and Zinc for Age-Related Degeneration and Vision Loss", Arch Ophthalmol, Oct. 2001; 119(10): 1417-1436.
Andrew Forge et al., "Aminoglycoside Antibiotics", Audiol Neurootol 2000; 5:3-22.

(56) References Cited

OTHER PUBLICATIONS

Roman A. Eliseev et al., "Bcl-2 and tBid proteins counter-regulate mitochondrial potassium transport", Biochimica et Biophysica Acta 1604 (2003) 1-5.
Xue Wang et al., "Bcl-XL disrupts death-inducing signal complex formation in plasma membrane induced by hypoxia/reoxygenation", The FASEB Journal, Research Communication, pp. 1826-183, 2004.
Kulawiak et al., "BK channel openers inhibit ROS production of isolated rat brain mitochondria", Experimental Neurology 212, 2008, pp. 543-547.
Siemen et al., "CA 2+-Activated K Channel of the BK-Type in the Inner Mitochondrial Membrane of a Human Glioma Cell Line", Biochemical and Biophysical Research Communications, 257, 1999, pp. 549-554.
Carnevali et al., "Cigarette smoke extract induced oxidative stress and apoptosis in human lung fibroblasts", Am J Physiol Lung Cell Mol Physiol 284, 2003, pp. L955-L963.
Schafer et al., "Comparing Beta-Carotene, Vitamin E and Nitric Oxide as Membrane Antioxidants", Biol. Chem. vol. 383, Mar./Apr. 2002, pp. 671-681.
Kelsell et al., "Connexin 26 mutations in hereditary non-syndromic sensorineural deafness", Letters to Nature, vol. 387, May 1997, pp. 80-83.
Piwonska et al., "Differential Distribution of Ca 2+-Activated Potassium Channel Beta 4 Subunit in Rat Brain: Immunolocalization in Neuronal Mitochondria", Neuroscience 153, 2008, pp. 446-460.
Le Prell et al., "Electromotile hearing: Acoustic tones mask psychophysical response to high-frequency electrical stimulation of intact guinea pig cochlea", J, Acoust. Soc. Am. 120 (6), Dec. 2006, pp. 3889-3900.
Nele Hilgert et al., "Forty-six genes causing nonsyndomic hearing impairment: Which ones should be analyzed in DNA diagnostics?", Mutation Research 681 (2009) pp. 189-196.
Kikuchi et al., "Gap junction systems in the mammalian cochlea", Brain Research Reviews 32, 2000, pp. 163-166.
Agustin D. Martinez et al., "Gap-Junction Channel Dysfunction in Deafness and Hearing Loss," Antioxidants & Redox Signaling, vol. 11, No. 2, 2009.
Ohinata et al., "Glutathione limits noise-induced hearing loss", Hearing Research 146, 2000, pp. 28-34.
Wang et al., "Hepatocyte Growth Factor Protects against Hypoxia/Reoxygenation-induced Apoptosis in Endothelial Cells", The Journal of Biological Chemistry, vol. 279, No. 7, Feb. 13, 2004, pp. 5237-5243.
Budinger et al., "Hyperoxia-induced Apoptosis Does Not Require Mitochondrial Reactive Oxygen Species and Is Regulated by Bcl-2 Proteins", The Journal of Biological Chemistry, vol. 277, No. 18, May 3, 2002, pp. 15654-15660.
Burton et al., "Is Vitamin E the Only Lipid-Soluble, Chain-Breaking Antioxidant in Human Blood Plasma and Erythrocyte Membranes?", Archives of Biochemistry and Biophysics, vol. 221, No. 1, Feb. 15, 1983, pp. 281-290.
Wangemann, "K+ Cycling and Its Regulation in the Cochlea and the Vestibular Labyrinth", Audiol Neurootol 2002; 7: 199-205.
Niki, "Lipid antioxidants: How they may act in biological systems", Br. J. Cancer (1987), 55, Suppl. VIII, pp. 153-157.
Ryter et al., "Comprehensive Invited Review: Mechanisms of Cell Death in Oxidative Stress", Antioxidants & Redox Signaling, vol. 9, No. 1, 2007, pp. 49-89.
Bednarczyk et al., "New Properties of mitochondrial ATP-regulated potassium channels", J. Bionerg Biomembr, 2008, 40, pp. 325-335.
Altura et al., "Noise-induced hypertension and magnesium in rats: relationship to microcirculation and calcium", J Appl Physiol, 1992, 72, pp. 194-202.
Rybak et al., "Ototoxicity", Kidney International (2007) 72, 931-935.
Ames et al., "Oxidants, antioxidants, and the degenerative diseases of aging", Proc. Natl. Acad. Sci. USA, Sep. 1993, vol. 90, pp. 7915-7922.
Zhao et la., "Oxidative damage pathways in relation to normal tissue injury", The British Journal of Radiology, 80, 2007, pp. S23-S31.
Coyle et al., "Pendred syndrome (goitre and sensorineural hearing loss) maps to chromosome 7 in the region containing the nonsyndromic deafness gene DFNB4", Apr. 1996, Nature Genetics, vol. 12, pp. 421-423.
Hilgert et al., "Phenotypic variability of patients homozygous for the GJB2 mutation 35delG cannot be explained by the influence of one major modifier gene", European Journal of Human Genetics, 2009, 17, pp. 517-524.
Agarwal et al., "Phospholipase Activation Triggers Apoptosis in Photosensitized Mouse Lymphoma Cells", Cancer Research 53, Dec. 15, 1993, pp. 5897-5902.
Yu, "Regulation and critical role of potassium homeostasis in apoptosis", Progress in Neurobiology 70, 2003, pp. 363-386.
Godar et al., "Spectral Dependence of UV-Induced Immediate and Delayed Apoptosis: The Role of Membrane and DNA Damage", Photochemistry and Photobiology, vol. 62, No. 1, 1995, pp. 108-113.
Wang et al., "Tanshinone (*Salviae miltiorrhizae* Extract) Preparations Attenuate Aminoglycoside-Induced Free Radical Formation in Vitro and Ototoxicity in Vivo", Antimicrobial Agents and Chemotherapy, Jun. 2003, vol. 47, No. 6, pp. 1836-1841.

* cited by examiner

| Table Analyzed | Control Group | | Control Group | |
|---|---|---|---|---|
| Column A | 12 kHz 4wk | | 16 kHz 4wk | |
| Vs | vs | | vs | |
| Column B | 12 kHz 16wk | | 16 kHz 16wk | |
| | | | | |
| Paired t test | | | | |
| P value | 0.2370 | | 0.2148 | |
| P value summary | ns | | ns | |
| Are means significantly different? (P < 0.05) | No | | No | |
| One- or two-tailed P value? | One-tailed | | One-tailed | |
| t, df | t=0.7567 df=7 | | t=0.8382 df=7 | |
| Number of pairs | 8 | | 8 | |
| | | | | |
| How big is the difference? | | | | |
| Mean of differences | -1.750 | | -2.250 | |
| 95% confidence interval | -7.219 to 3.719 | | -8.598 to 4.098 | |
| R square | 0.07562 | | 0.09122 | |
| | | | | |
| How effective was the pairing? | | | | |
| Correlation coefficient (r) | -0.01614 | | 0.3088 | |
| P Value (one tailed) | 0.4849 | | 0.2284 | |
| P value summary | ns | | ns | |
| Was the pairing significantly effective? | No | | No | |
| | 12k - 4 vs. 16 wk | | 16k -- 4 vs. 16 wk | |
| Number of values | 8 | 8 | 8 | 8 |
| | | | | |
| Minimum | 85.00 | 82.00 | 82.00 | 85.00 |
| 25% Percentile | 85.25 | 87.25 | 83.50 | 85.00 |
| Median | 87.00 | 90.00 | 90.50 | 89.00 |
| 75% Percentile | 90.75 | 94.25 | 92.00 | 94.50 |
| Maximum | 98.00 | 97.00 | 95.00 | 107.0 |
| | | | | |
| Mean | 88.38 | 90.13 | 88.75 | 91.00 |
| Std. Deviation | 4.470 | 4.704 | 4.773 | 7.559 |
| Std. Error | 1.580 | 1.663 | 1.688 | 2.673 |
| | | | | |
| Lower 95% CI | 84.64 | 86.19 | 84.76 | 84.68 |
| Upper 95% CI | 92.11 | 94.06 | 92.74 | 97.32 |

*Figure 15*

| Table Analyzed | ACEMg Group | | ACEMg Group | |
|---|---|---|---|---|
| Column A | 12 kHz 4wk | | 16 kHz 4wk | |
| Vs | vs | | vs | |
| Column B | 12 kHz 16wk | | 16 kHz 16wk | |
| | | | | |
| Paired t test | | | | |
| P value | 0.0029 | | < 0.0001 | |
| P value summary | ** | | **** | |
| Are means significantly different? (P < 0.05) | Yes | | Yes | |
| One- or two-tailed P value? | One-tailed | | One-tailed | |
| t, df | t=4.613 df=5 | | t=11.82 df=5 | |
| Number of pairs | 6 | | 6 | |
| | | | | |
| How big is the difference? | | | | |
| Mean of differences | 13.67 | | 11.00 | |
| 95% confidence interval | 6.049 to 21.28 | | 8.607 to 13.39 | |
| R square | 0.8097 | | 0.9654 | |
| | | | | |
| How effective was the pairing? | | | | |
| Correlation coefficient (r) | 0.8487 | | 0.9663 | |
| P Value (one tailed) | 0.0817 | | 0.0008 | |
| P value summary | ns | | *** | |
| Was the pairing significantly effective? | No | | Yes | |
| | 12k - 4 vs. 16 wk | | 16k – 4 vs. 16 wk | |
| Number of values | 6 | 6 | 6 | 6 |
| | | | | |
| Minimum | 93.00 | 75.00 | 88.00 | 75.00 |
| 25% Percentile | 94.50 | 77.25 | 88.00 | 77.25 |
| Median | 98.50 | 82.50 | 97.50 | 88.00 |
| 75% Percentile | 100.0 | 88.75 | 106.3 | 94.00 |
| Maximum | 100.0 | 100.0 | 107.0 | 97.00 |
| | | | | |
| Mean | 97.50 | 83.83 | 97.33 | 86.50 |
| Std. Deviation | 3.017 | 8.841 | 8.430 | 9.072 |
| Std. Error | 1.232 | 3.609 | 3.442 | 3.704 |
| | | | | |
| Lower 95% CI | 94.33 | 74.56 | 88.49 | 76.98 |
| Upper 95% CI | 100.7 | 93.11 | 106.2 | 96.02 |

*Figure 16*

| Table Analyzed | BL (4 weeks of age) | | | |
|---|---|---|---|---|
| Column A or D | Cntrl 12k BL | | Cntrl 16k BL | |
| vs | vs | | vs | |
| Column G or H | ACEMg 12k BL | | ACEMg 16k BL | |
| | | | | |
| Unpaired t test | | | | |
| P value | 0.0005 | | 0.0160 | |
| P value summary | *** | | * | |
| Are means significantly different? (P < 0.05) | Yes | | Yes | |
| One- or two-tailed P value? | One-tailed | | One-tailed | |
| t, df | t=4.299 df=12 | | t=2.426 df=12 | |
| | | | | |
| How big is the difference? | | | | |
| Mean ± SEM of column A | 88.38 ± 1.580 N=8 | | 88.75 ± 1.688 N=8 | |
| Mean ± SEM of column G | 97.50 ± 1.232 N=6 | | 97.33 ± 3.442 N=6 | |
| Difference between means | -9.125 ± 2.123 | | -8.583 ± 3.537 | |
| 95% confidence interval | -13.75 to -4.500 | | -16.29 to -0.8753 | |
| R square | 0.6063 | | 0.3291 | |
| | | | | |
| F test to compare variances | | | | |
| F,DFn, Dfd | 2.196, 7, 5 | | 3.119, 5, 7 | |
| P value | 0.4036 | | 0.1702 | |
| P value summary | ns | | ns | |
| Are variances significantly different? | No | | No | |
| | | | | |
| Number of values | 8 | 6 | 8 | 6 |
| | | | | |
| Minimum | 85.00 | 93.00 | 82.00 | 88.00 |
| 25% Percentile | 85.25 | 94.50 | 83.50 | 88.00 |
| Median | 87.00 | 98.50 | 90.50 | 97.50 |
| 75% Percentile | 90.75 | 100.0 | 92.00 | 106.3 |
| Maximum | 98.00 | 100.0 | 95.00 | 107.0 |
| | | | | |
| Mean | 88.38 | 97.50 | 88.75 | 97.33 |
| Std. Deviation | 4.470 | 3.017 | 4.773 | 8.430 |
| Std. Error | 1.580 | 1.232 | 1.688 | 3.442 |
| | | | | |
| Lower 95% CI | 84.64 | 94.33 | 84.76 | 88.49 |
| Upper 95% CI | 92.11 | 100.7 | 92.74 | 106.2 |

*Figure 17*

| Table Analyzed | mOHC across cochlea |
|---|---|
| Column H | ACEMg OHC |
| Vs | vs |
| Column I | Control OHC |
| | |
| Unpaired t test | |
| P value | 0.0439 |
| P value summary | * |
| Are means significantly different? (P < 0.05) | Yes |
| One- or two-tailed P value? | One-tailed |
| t, df | t=1.835 df=14 |
| | |
| How big is the difference? | |
| Mean ± SEM of column H | 58.56 ± 6.092 N=8 |
| Mean ± SEM of column I | 75.17 ± 6.695 N=8 |
| Difference between means | -16.61 ± 9.051 |
| 95% confidence interval | -36.02 to 2.807 |
| R square | 0.1939 |
| | |
| F test to compare variances | |
| F,DFn, Dfd | 1.208, 7, 7 |
| P value | 0.8096 |
| P value summary | ns |
| Are variances significantly different? | No |

| | ACEMg OHC | Control OHC |
|---|---|---|
| Number of values | 8 | 8 |
| | | |
| Minimum | 36.30 | 48.03 |
| 25% Percentile | 45.49 | 54.83 |
| Median | 52.68 | 84.17 |
| 75% Percentile | 73.89 | 90.93 |
| Maximum | 87.77 | 92.57 |
| | | |
| Mean | 58.56 | 75.17 |
| Std. Deviation | 17.23 | 18.94 |
| Std. Error | 6.092 | 6.695 |
| | | |
| Lower 95% CI | 44.15 | 59.34 |
| Upper 95% CI | 72.96 | 91.00 |

*Figure 18*

| Table Analyzed | mIHC across cochlea |
|---|---|
| Column K | ACEMg IHC |
| vs | vs |
| Column L | Control IHC |
| | |
| Unpaired t test | |
| P value | < 0.0001 |
| P value summary | **** |
| Are means significantly different? (P < 0.05) | Yes |
| One- or two-tailed P value? | One-tailed |
| t, df | t=5.067 df=14 |
| | |
| How big is the difference? | |
| Mean ± SEM of column K | 1.870 ± 1.234 N=8 |
| Mean ± SEM of column L | 25.51 ± 4.499 N=8 |
| Difference between means | -23.64 ± 4.666 |
| 95% confidence interval | -33.65 to -13.63 |
| R square | 0.6471 |
| | |
| F test to compare variances | |
| F,DFn, Dfd | 13.30, 7, 7 |
| P value | 0.0029 |
| P value summary | ** |
| Are variances significantly different? | Yes |

| | ACEMg IHC | Control OHC |
|---|---|---|
| Number of values | 8 | 8 |
| | | |
| Minimum | 0.0 | 0.7600 |
| 25% Percentile | 0.0 | 16.91 |
| Median | 0.1350 | 28.50 |
| 75% Percentile | 2.478 | 34.83 |
| Maximum | 10.12 | 39.28 |
| | | |
| Mean | 1.870 | 25.51 |
| Std. Deviation | 3.490 | 12.73 |
| Std. Error | 1.234 | 4.499 |
| | | |
| Lower 95% CI | -1.048 | 14.87 |
| Upper 95% CI | 4.788 | 36.15 |

*Figure 19*

| Table Analyzed | Threshold shifts | | | |
|---|---|---|---|---|
| Column A or D | 12k Control | | 16k Control | |
| Vs | vs | | vs | |
| Column B or E | 12k ACEMg | | 16k ACEMg | |
| | | | | |
| Unpaired t test | | | | |
| P value | 0.0007 | | 0.0007 | |
| P value summary | *** | | *** | |
| Are means significantly different? (P < 0.05) | Yes | | Yes | |
| One- or two-tailed P value? | One-tailed | | One-tailed | |
| t, df | t=4.168 df=12 | | t=4.101 df=12 | |
| | | | | |
| How big is the difference? | | | | |
| Mean ± SEM of column A | 1.750 ± 2.313 N=8 | | 2.250 ± 2.684 N=8 | |
| Mean ± SEM of column G | -13.67 ± 2.963 N=6 | | -11.00 ± 0.9309 N=6 | |
| Difference between means | 15.42 ± 3.699 | | 13.25 ± 3.231 | |
| 95% confidence interval | 7.357 to 23.48 | | 6.210 to 20.29 | |
| R square | 0.5915 | | 0.5836 | |
| | | | | |
| F test to compare variances | | | | |
| F,DFn, Dfd | 1.231, 5, 7 | | 11.09, 7, 5 | |
| P value | 0.7728 | | 0.0175 | |
| P value summary | ns | | * | |
| Are variances significantly different? | No | | Yes | |
| | | | | |
| Number of values | 8 | 6 | 8 | 6 |
| | | | | |
| Minimum | -10.00 | -22.00 | -8.000 | -13.00 |
| 25% Percentile | -2.250 | -16.75 | -5.000 | -13.00 |
| Median | 1.500 | -15.00 | 2.500 | -11.50 |
| 75% Percentile | 8.000 | -11.25 | 5.750 | -9.250 |
| Maximum | 10.00 | 0.0 | 16.00 | -7.000 |
| | | | | |
| Mean | 1.750 | -13.67 | 2.250 | -11.00 |
| Std. Deviation | 6.541 | 7.257 | 7.592 | 2.280 |
| Std. Error | 2.313 | 2.963 | 2.684 | 0.9309 |
| | | | | |
| Lower 95% CI | -3.719 | -21.28 | -4.097 | -13.39 |
| Upper 95% CI | 7.219 | -6.051 | 8.597 | -8.607 |

*Figure 20*

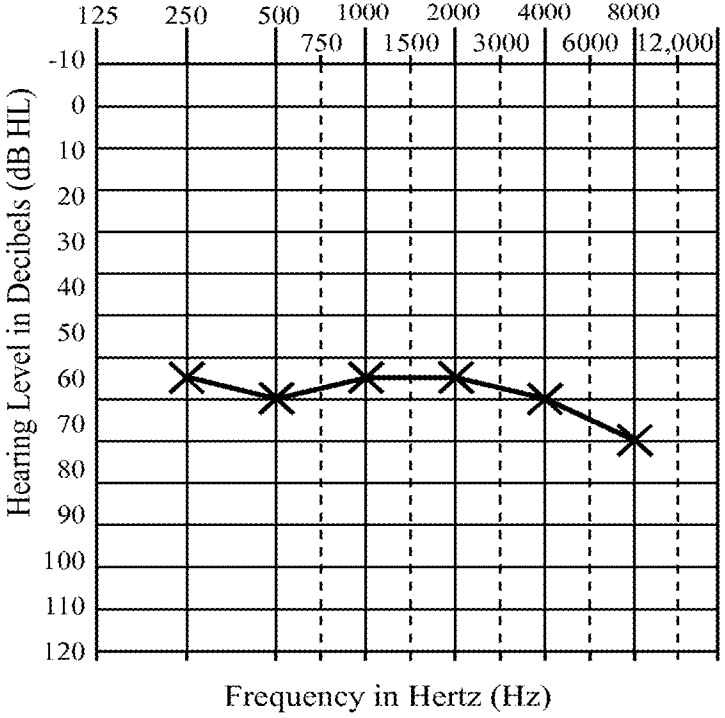
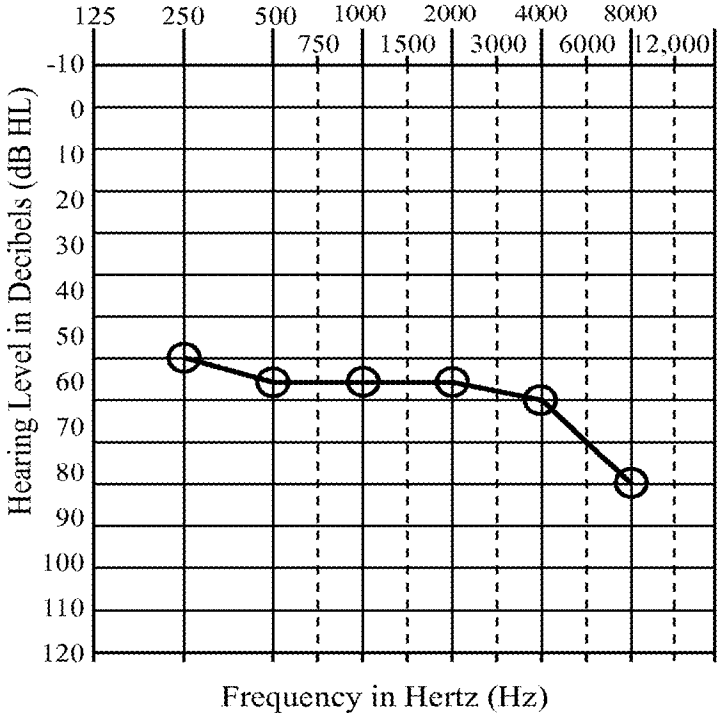
FIG. 21C

METHOD FOR TREATING HEARING LOSS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

[This application is a continuation-in-part of U.S. patent application Ser. No. 13/091,931, filed Apr. 21, 2011, which is a continuation-in-part of U.S. application Ser. No. 12/761,121 filed on Apr. 15, 2010, which is a continuation-in-part of U.S. application Ser. No. 11/623,888, filed on Jan. 17, 2007. U.S. application Ser. No. 11/623,888 is now U.S. Pat. No. 7,951,845, and U.S. application Ser. No. 11/623,888 claims priority to and all advantages of U.S. Provisional Patent App. Ser. No. 60/760,055, which was filed on Jan. 19, 2006. This patent application is also a continuation-in-part of U.S. application Ser. No. 13/091,931 filed on Apr. 21, 2011, which is a continuation of U.S. application Ser. No. 11/623,888 filed on Jan. 17, 2007. U.S. application Ser. No. 11/623,888 is now U.S. Pat. No. 7,951,845, and U.S. application Ser. No. 11/623,888 claims priority to and all advantages of U.S. Provisional Patent App. Ser. No. 60/760,055 filed on Jan. 19, 2006.] *This application is a reissue of Ser. No. 13/839,760 which is a continuation-in-part of application Ser. No. 13/679,224 filed on Nov. 16, 2012, now U.S. Pat. No. 8,927,528 which is a continuation-in-part of Ser. No. 12/761,121 filed on Apr. 15, 2010, now U.S. Pat. No. 8,338,397, which is a continuation-in-part of Ser. No. 11/623,888 filed on Jan. 17, 2007, now U.S. Pat. No. 7,951,845, which claims benefit of 60/760,055 filed on Jan. 19, 2006, and said Ser. No. 13/679,224 filed on Nov. 16, 2012 is a continuation-in-part of Ser. No. 13/091,931 filed on Apr. 21, 2011, now U.S. Pat. No. 8,338,398 which is a continuation of Ser. No. 11/623,888 filed on Jan. 17, 2007, now U.S. Pat. No. 7,951,845 which claims benefit of 60/760,055 filed on Jan. 19, 2006.*

GOVERNMENT LICENSE RIGHTS

This disclosure was made with government support under DC004058 awarded by the National Institutes of Health. The government has certain rights in the disclosure.

BACKGROUND OF THE DISCLOSURE

1. Field of the Disclosure

The present disclosure generally relates to method for treating hearing loss. More specifically, the method includes administering a composition to the mammal, wherein the composition consists essentially of a biologically effective amount of vitamin A, vitamin E, vitamin C, a vasodilator comprising magnesium, and, optionally, a withanolide, and/or resveratrol.

2. Description of the Related Art

Extensive studies have been performed on compositions for treating side effects to antibiotic treatment, along with methods of treating the side effects using various compositions. Particularly problematic side effects from antibiotic treatment include kidney damage, loss of balance, and hearing loss attributable to antibiotic treatment such as aminoglycoside or glycopeptide antibiotic treatments. The damaging side effects of many aminoglycoside antibiotics were first reported in the 1940s, and the damaging side effects have long been an impediment to use of aminoglycoside antibiotics. Aminoglycoside antibiotics cause permanent deficits in the vestibular system (balance) and irreversible cell death in the cochlea, resulting in hearing impairment.

While the damaging side effects of aminoglycoside antibiotics, in particular, have impeded their use, it has not eliminated their use. Aminoglycoside antibiotics are the only "standard of treatment" in certain severe gram-negative bacterial infections, and the only inexpensive antibiotics that are available in developing countries. In the USA and European countries where the side effects are well recognized, and where $2^{nd}$ and $3^{rd}$ generation antibiotics are substituted wherever possible, side effects such as inner ear damage and hearing loss in patients can be minimized through careful monitoring of aminoglycoside antibiotic treatment. However, in countries in which there are fewer alternative drugs and monitoring is less rigorous or nonexistent, side effects associated with aminoglycoside antibiotic treatment is more prevalent.

Notably, HIV death is often driven by tuberculosis as a secondary infection to HIV. In developing countries, aminoglycoside antibiotic treatment is widely used against tuberculosis. Given the generally lax monitoring and the high incidence of side effects associated with aminoglycoside antibiotic treatment in developing countries, poor patient compliance in completing proscribed aminoglycoside antibiotic treatment is common, contributing to the development of drug-resistant strains of tuberculosis.

Historically, from the first identification of side effects such as hearing loss attributable to aminoglycoside antibiotic treatment in the 1940s, research focused on identification of the aminoglycoside-induced pathophysiology and otohistopathology, the pharmacokinetics of the aminoglycoside antibiotics, and methods of monitoring early damage and thereby avoiding serious side effects attributable to aminoglycoside antibiotic treatment in humans. Mechanistic studies of aminoglycoside ototoxicity began in the 1980s. Findings that free-radical formation played a role in aminoglycoside ototoxicity were first indicated by reports of efficacy of some free radical scavengers in reducing ototoxicity. More direct evidence was uncovered in the mid to late 1990s of free radical formation by gentamicin (which is one type of aminoglycoside antibiotic), while ototoxicity attributable to aminoglycoside treatment was found to be inversely related to glutathione levels (endogenous antioxidant) in inner ear tissues. It has since been shown that ototoxicity of aminoglycoside antibiotics could be reduced by treatment with some radical scavengers.

Free radical formation has been shown to play a role in many instances of stress-induced cell pathology. High intensity noise has been shown to induce free radical formation. For the inner ear, the mechanism by which high intensity noise induces cell death in the cochlea and hearing impairment has been shown to be dependent on free radical formation. Noise-induced trauma to the inner ear has been shown to be inversely related to endogenous levels of glutathione in cochlear tissues.

The parallels between the mechanisms of noise- and antibiotic-induced cell death in the inner ear suggest that they share a common cell death pathway such that it is natural to speculate that agents found effective to attenuate noise-induced hearing loss may be effective to attenuate antibiotic-induced hearing loss. However, it is clear from the literature that great variability is found in the efficacy of some of the agents to reduce the damaging side effects of aminoglycoside antibiotics. To some extent, the variable efficacy may reflect differential mechanisms of action of the scavengers or unique molecular structures of the free radicals formed. Some agents have been tested for efficacy against noise-induced hearing loss (NIHL) and their relative efficacy has been found to differ from their relative efficacy for drug-induced hearing loss. For example, allopurinol is ineffective in reducing gentamicin-induced ototoxicity, but is effective in reducing noise-induced hearing loss. Given such observations (and other similar ones in literature), there is no substantial basis for believing that a formulation for treating noise-induced hearing loss will be effective to treat antibiotic-induced hearing loss and other side effects of antibiotic treatment.

In view of the foregoing, there remains further opportunities to develop effective methods of treating side effects of antibiotic treatment, including antibiotic-induced hearing loss, kidney damage, and loss of balance, the methods including the step of administering a composition that includes a specific combination of components, in biologically effective amounts, in conjunction with administration of antibiotics that are capable of causing side effects such as hearing loss in mammals.

There is also an opportunity to provide a composition and a method of treating hearing loss including the step of administering the composition that includes a specific combination of components having an additive effect that is equal to or greater than the sum of the effect of the individual components in treating hearing loss when used in biologically effective amounts.

SUMMARY OF THE DISCLOSURE

The subject disclosure provides a method of treating hearing loss includes the step administering a composition to the mammal, wherein the composition consists essentially of a biologically effective amount of vitamin A, vitamin E, vitamin C, a vasodilator comprising magnesium, and, optionally, a withanolide, and/or resveratrol.

BRIEF DESCRIPTION OF THE DRAWINGS

Other advantages of the present disclosure will be readily appreciated, as the same becomes better understood by reference to the following detailed description when considered in connection with the accompanying drawings wherein:

FIGS. 15-18 are tables that set forth the results of the statistical analysis of the Examples. These tables include the mean ABR thresholds Cx26 mice in the Control Group at baseline and 12 weeks post diet for each test frequency [no significant difference], the similar analysis for the ACEMg Group [significant difference found], analysis of the difference in baseline mean thresholds for the Control and ACEMg groups at each test frequency [significant difference observed] and analysis of the mean threshold shifts observed in the ACEMg group vs the control group at each test frequency [highly significant difference observed].

FIGS. 19 and 20 are tables that set forth the results of statistical analysis for the surviving inner and outer hair cells in the Cx26 mice in the Control Group vs the ACEMg treated group of the Examples.

FIG. 21C is an audiogram showing speech reception thresholds of Right 65 dB and Left 65 dB of the human subject of the Examples, after treatment, at approximately 11 years of age;

DETAILED DESCRIPTION

Figure 1:
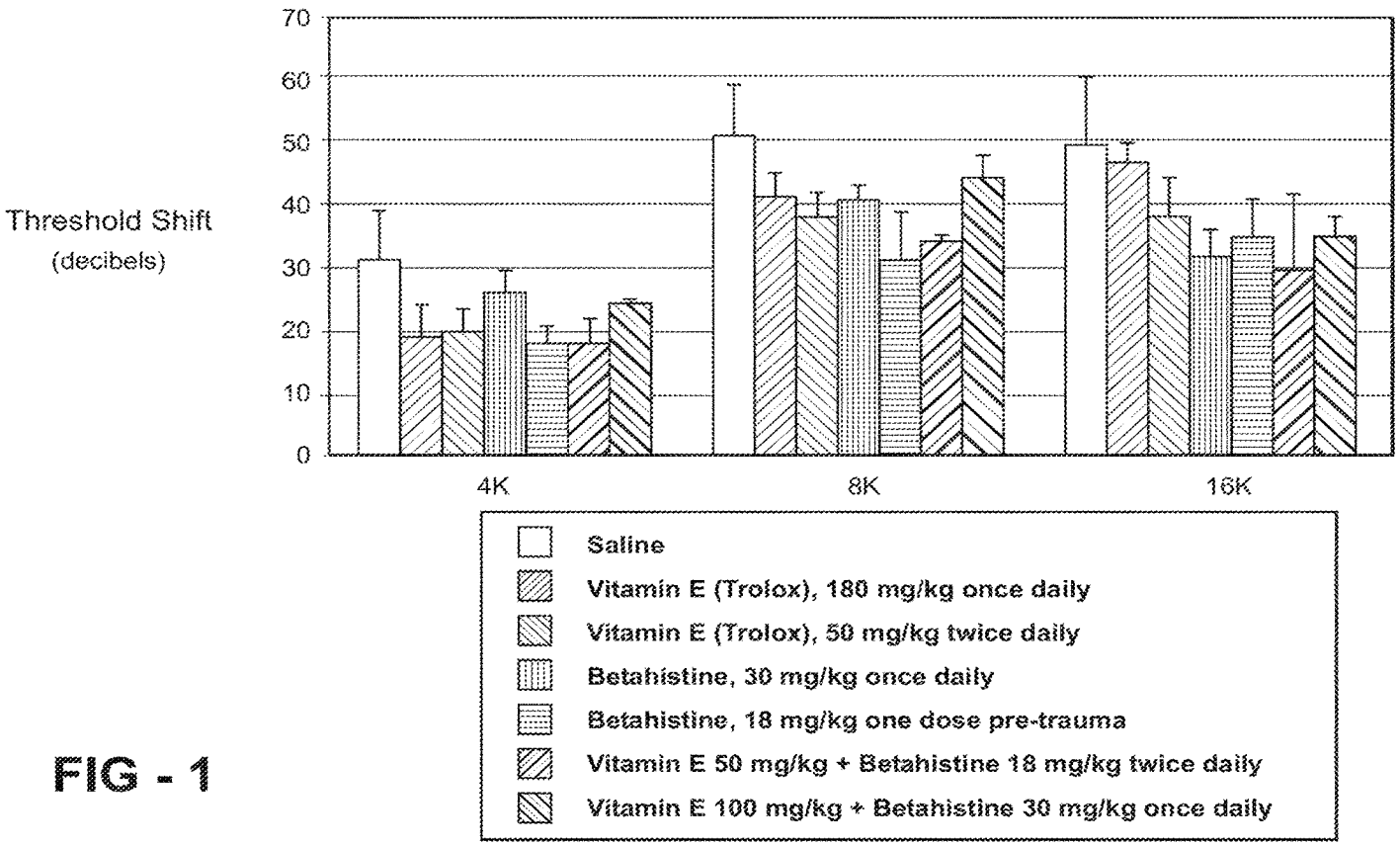
FIG. 1 is a graph showing the effect of a Comparative Example of a composition used to treat hearing loss including Trolox® (vitamin E) and betahistine on reduction of a threshold shift in guinea pigs from baseline threshold sensitivity at 4, 8, and 16 kHz after exposure to 120 decibel SPL Octave Band Noise centered at 4 kHz for five hours.

A composition for treating hearing loss includes components that may function through different biological mechanisms to provide an additive effect that is equal to or greater than a sum of the effect of the individual components. The composition is typically used for treating hearing loss resulting from trauma to an inner ear of a mammal. The trauma may be further defined as mechanically-induced metabolic trauma, mechanical/metabolic trauma, stress trauma, stress-induced damage, or environmental stress. However, it is also possible that the composition may also be used to treat or prevent other types of hearing loss, including, for example, age-related hearing loss, antibiotic-induced hearing loss, and chemotherapeutic-induced hearing loss. The composition may further be used to prevent hearing loss during restoration surgery performed on the inner ear.

Further, a method in accordance with the instant disclosure includes the step of administering a composition to a mammal that includes components that function through different biological mechanisms. The composition is typically used for treating hearing loss resulting from trauma to the inner ear of a mammal. However, as described in further detail below, the composition can be administered in conjunction with administration of an antibiotic and can be used to treat various side effects of the antibiotic treatment. The trauma to the inner ear of the mammal may be further defined as mechanically-induced metabolic trauma, mechanical/metabolic trauma, stress trauma, stress-induced damage, or environmental stress. In the context of the instant disclosure, the composition is used to treat or prevent side effects of antibiotic treatment including antibiotic-induced hearing loss. The composition may further be used to prevent hearing loss during restoration surgery performed on the inner ear.

It has been found that one result of noise trauma, or other stressors such as age and drugs such as antibiotics as set forth above, is that free radicals form in association with metabolic trauma. The free radicals damage sensitive structures, such as hair cells, within the ear. Vasoconstriction also occurs as a result of the noise, which leads to decreased blood flow to the inner ear and causes cell death that results in hearing loss. It has been found that the underlying cause of vasoconstriction is noise-induced free radical formation. Specifically, one of the molecules formed in the inner ear as a result of the presence of free radicals is 8-isoprostane-2F alpha, which is a bioactive agent. The bioactive agent induces a constriction of blood vessels in the inner ear, which causes a reduction in blood flow. In order to counteract the free radical formation and the vasoconstriction, the composition of the subject disclosure includes at least one scavenger of singlet oxygen, a donor antioxidant, a third antioxidant, and a vasodilator. Unexpectedly, it was found that the composition including the at least one scavenger of singlet oxygen, the donor antioxidant, the third antioxidant, and the vasodilator produce an additive effect that is not only greater than the effect of any one of those components alone, but at least equal to or greater than a sum of the effects of each of the components when used to treat noise-induced hearing loss. Similar effectiveness has also been found when the composition is used to treat side effects of antibiotic treatment including antibiotic-induced hearing loss.

It is believed that genetic hearing disorders may be dependent upon a defect in a single gene leading to hearing impairment or deafness (e.g. nonsyndromic hearing loss, approximately 70% of inherited childhood deafness). Alternatively, hearing loss may be dependent upon mutations in more than one gene and may be associated with other inherited clinical disorders (e.g. syndromic).

The most common syndromal deafness, accounting for as much as 10% of all hereditary hearing loss, is Pendred syndrome, which has been localized to chromosome 7q31 containing the SLC26A4 gene. The most common nonsyndromic hearing loss is based on a defect in the Connexin 26 (CX26) protein. Approximately 100 specific Connexin 26 mutations have been identified, together accounting for approximately 50% of recessively inherited nonsyndromic hearing impairment.

More specifically, mutations in the gene encoding Connexin 26 can cause hearing loss that is typically stable, but may be progressive. Connexins are transmembrane proteins, expressed in non-sensory cells of the inner ear that create intercellular channels between adjoining plasma membranes of adjacent cells, with a small (2-3 nm) gap between each protein (gap junction). The reason for progression of hearing loss is unknown, but may involve common pathways for otologic insults causing hearing loss. Theoretically, the loss of Connexin 26 reduces the ability of supporting cells to shuttle metabolic products involved in sound transduction. This change tends to increase the oxidative stress for hair cells and supporting cells, both of which die in Connexin 26 deafness.

Alternatively, or additionally, the hearing loss may reflect a defect in the gap junction beta 2 (GJB2) gene resulting in flawed gene copies which mis-instructs production of the Connexin 26 protein. This typically results in disruption of the potassium metabolism, distribution and movement in the inner ear and particularly in the supporting cells, and a disruption of cellular homeostasis in these cells, frequently leading to cell death.

Since potassium homeostasis in the inner ear and health of supporting cells is typically important for normal function of the sensory cells of the inner ear (hair cells), any disruption tends to result in hearing impairment. In one example, mouse models of the Connexin 26 defect show early widespread degeneration of both inner and outer hair cells, presumably secondary to the supporting cell gap junction defect. In humans, hearing impairment may begin sometime following birth and progress until profound deafness occurs. However, the gene defect may be expressed as mild to moderate hearing impairment.

More specifically, one or more defects in the Connexin 26 gene may lead to disruption of potassium homeostasis in an inner ear of a mammal. Potassium homeostasis may regulate apoptosis such that connexin-driven disruption of inner ear potassium homeostasis may lead to increase production of free radicals by mitochondria directly leading to upregulation of apoptotic cell death pathways as well as support direct potassium induced cytochrome c release and apoptosis. Potassium channels Kv1.3, mitochondrial $Ca^{2+}$ regulated potassium channel, mitoBKCa, and mitochondrial ATP-regulated potassium channel—mitoKATP have been demonstrated in mitochondrial membranes. Mitochondrial potassium channels effect energy production by the mitochondrion. In addition, there may be a direct dependence of free radical formation on potassium channel function during the respiratory chain in mitochondrial function. Moreover, increased mitochondrial K+ influx may result in release of cytochrome c and caspase-3 followed by apoptosis. These events could be blocked by bcl-2, which upregulated the mitochondrial K/H-exchanger, leading to increased removal of K. In addition, Bcl-2 and tBid proteins may counter-regulate mitochondrial potassium transport.

Antioxidants act through a variety of mechanisms. The at least one scavenger of singlet oxygen and the donor antioxidant are two different classes of antioxidants that act through different mechanisms. The third antioxidant, while typically a scavenger of singlet oxygen, may be a different antioxidant that acts through a different mechanism. Scavengers of singlet oxygen reduce free radicals that contribute to hearing loss and other side effects of antibiotic treatment such as kidney damage and loss of balance. More specifically, by reducing free radicals, the scavengers of singlet oxygen prevent, among other damaging effects, the singlet oxygen from reacting with lipids to form lipid hydroperoxides. Lipid hydroperoxides play a role in causing hearing loss.

Even within the class of scavengers of singlet oxygen, it is believed that various antioxidants react at different sites within the body, and in particular, within cells to attenuate free radical formation. For example, one of the scavengers of singlet oxygen is typically vitamin A. In various non-limiting embodiments described herein, the terminology Vitamin A and beta-carotene may be used interchangeably. However, these embodiments in no way limit this disclosure. Vitamin A is a generic term that captures a number of molecules with a biological activity of retinol or carotenoids. Primary dietary forms of vitamin A/retinol include retinol esters and beta-carotene. The beta-carotene is made up of a polyene chain of 11 conjugated double bonds with methyl branches spaced along the polyene chain, capped at both ends by cyclohexenyl rings with 1,1,5-trimethyl substitution. Other forms of vitamin A include xanxthophylls, astaxanthin, canthxanxin, lutein, and zeaxanthin, which include a backbone of beta-carotene with hydroxyl and/or carbonyl substitution on one or more of the cyclohexenyl rings. For purposes of the subject disclosure, the vitamin A is typically present as beta-carotene. Beta-carotene is a powerful scavenger of singlet oxygen, as well as nitric oxide and peroxynitrite, and may also scavenge lipid peroxyl radicals within a lipophilic compartment of a mitochondrial membrane. Beta-carotene is an excellent scavenger of free radicals under normal physiological conditions present in most tissues.

In addition to vitamin A, other scavengers of singlet oxygen may also be present in the composition of the subject disclosure. For example, another scavenger of singlet oxygen that may be present is resveratrol. Resveratrol is more efficient at scavenging hydroxyl radicals than vitamin C, and the addition of resveratrol to the vitamins A may have additive effects. The use of resveratrol in combination with other antioxidants (but not vitamins A, C, or E, and not the vasodilator magnesium or any other vasodilating substance), is known in the art to reduce age-related hearing loss.

The at least one scavenger of singlet oxygen is present in the composition in a biologically effective amount. For purposes of the subject disclosure, the biologically effective amount is further defined as an amount that is sufficient to produce an additive effect in a reduction in threshold shift when used in combination with other antioxidants and the magnesium. Additive effect, as used herein, refers to an effect that is equal to or greater than a sum of the effects of the individual components. In order to produce additive effect and the reduction in threshold shift, the at least one scavenger of singlet oxygen is typically present in the composition in a total amount of at least 830 international units (IU), more typically from 830 to 120,000 IU, most typically from about 2,100 to 70,000 IU for an adult dosage.

The amount of the vitamin A present in the composition is dependent upon the form of vitamin A that is used. For example, in one embodiment, vitamin A is present as retinol in an amount of at least 830 IU, more typically from 830 to 10,000 IU, more typically from 2,100 to 10,000 IU, most typically from 2,100 to 8,000 IU. As known in the art, a conversion of IU to weight for vitamin A (as retinol) is 3.33 IU/□g. Thus, at least 830 international units (IU) of vitamin A (as retinol) is equivalent to at least 0.25 mg of vitamin A, from 830 to 10,000 IU of vitamin A (as retinol) is equivalent to from 0.25 to 3 mg of vitamin A, and from 2,100 to 8,000 IU of vitamin A (as retinol) is equivalent to from 0.63 to 2.4 mg vitamin A.

Alternatively, the vitamin A may be present in the composition as beta-carotene, as opposed to retinol. The retinol activity equivalents (RAE) for retinol conversion to beta-carotene, which is a pro-vitamin A carotenoid, is 1 mg to 12 mg. In terms of conversion of the amounts set forth above for the vitamin A present in the composition as retinol to the vitamin A present in the composition as beta-carotene, in one example, a total amount of at least 3.0 mg or at least 830 international units (IU) of vitamin A as beta-carotene, more typically from 3.0 to 180 mg or 830 to 50,000 IU vitamin A as beta-carotene, most typically from about 7.2 to 108 mg or 2000 to 30,000 IU of vitamin A as beta-carotene is typically present for an adult dosage. In another example, a total amount of at least 3.0 mg or at least 10,000 international units (IU) of vitamin A as beta-carotene, more typically from 3.0 to 36 mg or 10,000 to 120,000 IU vitamin A as beta-carotene, most typically from about 7.5 to 21 mg or 25,000 to 70,000 IU of vitamin A as beta-carotene is typically present for an adult dosage.

Specific amounts of the vitamin A present in the composition may be dependent on the body weight of the mammal. In one specific example, the amount of vitamin A present as retinol in the composition is about 0.0178 mg/kg body weight. Thus, for an average human weighing about 70 kg, the amount of vitamin A present as retinol in the composition may be about 1.25 mg. If the vitamin A is in the form of beta-carotene, in one example, the beta carotene in the composition is about 0.257 mg/kg body weight may be present in an amount of about 18 mg. In another example, the beta-carotene in the composition may be about in an amount of about 15 mg.

It is to be appreciated that, when additional scavengers of singlet oxygen such as resveratrol are present in the composition in addition to vitamin A, the total amount of scavengers of singlet oxygen may be greater than the ranges set forth above for the at least one scavenger of singlet oxygen, so long as at least one scavenger of singlet oxygen is present in the amounts set forth above. In addition, other scavengers of singlet oxygen may be used in place of vitamin A, so long as the amount of the at least one scavenger of singlet oxygen is present within the amounts set forth above. When present, the resveratrol is typically included in the composition in an amount of at least 1 mg, more typically in an amount of from 10 mg to 1500 mg, most typically in an amount of from 15 mg to 1000 mg.

Whereas the at least one scavenger of singlet oxygen prevents the initial formation of lipid peroxides, the donor antioxidant reduces peroxyl radicals and inhibits propagation of lipid peroxidation that contributes to hearing loss. More specifically, the donor antioxidant reacts with and reduces peroxyl radicals and thus serves a chain-breaking function to inhibit propagation of lipid peroxidation. As is evident from the chain-breaking function of the donor antioxidant in lipid peroxidation, the donor antioxidant functions within cell membranes. A specific donor antioxidant that is contemplated for use in the composition of the subject disclosure is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopheral commercially available from Hoffman-Laroche, Ltd. of Basel, Switzerland, is a research agent that is typically used as a source of vitamin E.

The donor antioxidant is typically present in the composition, for example, in an amount of at least 75 IU, more typically from 75 IU to 2,000 IU, more typically from 150 to 1,500 IU, most typically from 150 IU to 800 IU. In another example, the donor antioxidant is present in the composition in an amount of at least 75 IU, more typically from 75 IU to 1,500 IU, most typically from 150 IU to 800 IU. As known in the art, a conversion of IU to weight for synthetic vitamin E is 0.66 mg/IU and for natural vitamin E is 0.45 mg/IU. Thus, when the donor antioxidant is synthetic vitamin E, in on example, at least 75 IU of vitamin E is equivalent to at least 50 mg of vitamin E, from 75 to 2,000 IU of synthetic vitamin E is equivalent to from 50 to 1,320 mg of vitamin E, from 150 to 1,500 IU of synthetic vitamin E is equivalent to from 100 to 1,000 mg of vitamin E, and from 150 to 800 IU of synthetic vitamin E is equivalent to from 100 to 536 mg of vitamin E. In another example, when the donor antioxidant is vitamin E, at least 75 IU of vitamin E is equivalent to at least 50 mg of vitamin E, from 75 to 1500 IU of vitamin E is equivalent to from 50 to 1000 mg of vitamin E, and from 150 to 800 IU of vitamin E is equivalent to from 150 to 600 mg of vitamin E. As with the amount and type of vitamin A, specific amounts of the vitamin E present in the composition may be dependent on the body weight of the mammal. In one specific example, the amount of synthetic vitamin E present in the composition is about 3.8 mg/kg body weight. Thus, for an average human weighing about 70 kg, the amount of vitamin E present in the composition may be about 266 mg. In another specific example, the amount of synthetic or natural vitamin E present in the composition is about 2.6 mg/kg body weight. Thus, for an average human weighing about 70 kg, the amount of vitamin E present in the composition may be about 182 mg.

In addition to the at least one scavenger of singlet oxygen and the donor antioxidant, the composition further includes the third antioxidant. While the third antioxidant may be a scavenger of singlet oxygen, the third antioxidant may also be an antioxidant that functions through a different mechanism. When the third antioxidant is a scavenger of singlet oxygen, the at least one scavenger of singlet oxygen is still present in the composition as a separate component from the third antioxidant, and is still present in the composition in the amounts set forth above for the at least one scavenger of singlet oxygen. As a result of the third antioxidant being another scavenger of singlet oxygen, the resulting composition would have at least two scavengers of singlet oxygen.

The third antioxidant is typically vitamin C, which is a scavenger of singlet oxygen and reactive nitrogen species. It is to be appreciated that, although the third antioxidant is typically vitamin C, other antioxidants may be used in place of the vitamin C, and the other antioxidants may function through different mechanisms than vitamin C. The term vitamin C applies to substances that possess antiscorbutic activity and includes two compounds and their salts: L-ascorbic acid (commonly called ascorbic acid) and L-dehydroascorbic acid. In addition to being known as ascorbic acid and L-ascorbic acid, vitamin C is also known as 2,3-didehydro-L-threo-hexano-1,4-lactone, 3-oxo-L-gulofuranolactone, L-threo-hex-2-enonic acid gamma-lactone, L-3 -keto-threo-hexuronic acid lactone, L-xylo-ascorbic acid and antiscorbutic vitamin. Vitamin C is known to scavenge both reactive oxygen species and reactive nitrogen species. It can be oxidized by most reactive oxygen and nitrogen species, including superoxide, hydroxyl, peroxyl and nitroxide radicals, as well as such non-radical reactive species as singlet oxygen, peroxynitrite and hypochlorite. Vitamin C thus inhibits lipid peroxidation, oxidative DNA damage, and oxidative protein damage.

In contrast to vitamin A, which functions best under conditions present in most tissues, water-soluble vitamin C is an excellent free radical scavenger in an aqueous phase to thus reduce free radicals at a site different from that of vitamin A. More specifically, ascorbic acid functions to reduce free radicals in fluid, such as in cytoplasmic fluid and/or blood, before the free radicals reach cell membranes.

The third antioxidant is typically present, for example, in an amount of at least 4,000 IU, more typically from 4,000 to 60,000, more typically from 8,000 to 40,000 IU, most typically from 8,000 to 20,000 IU. In another example, the third antioxidant is typically present in an amount of at least 4,000 IU, more typically from 6,000 to 40,000 IU, and most typically from 8,000 to 20,000 IU. Using vitamin C as an example for converting IU to weight units for the third antioxidant, as known in the art, a conversion of IU to weight for vitamin C is 0.05 mg/IU. Thus, at least 4,000 IU of vitamin C is equivalent to at least 200 mg of vitamin C, from 6,000 to 60,000 IU of vitamin C is equivalent to from 300 to 3,000 mg vitamin C, from 6,000 to 40,000 IU of vitamin C is equivalent to from 300 to 2,000 mg, from 8,000 to 40,000 IU of vitamin C is equivalent to from 400 to 2,000 mg vitamin C, and from 8,000 to 20,000 IU vitamin C is equivalent to from 400 to 1,000 mg vitamin C. As with vitamins A and E, specific amounts of the vitamin C or other third antioxidant present in the composition may be dependent on the body weight of the mammal. In one specific example, the amount of vitamin C present in the composition is about 7.14 mg/kg body weight. Thus, for an average human weighing about 70 kg, the amount of vitamin C present in the composition may be about 500 mg.

As set forth above, the composition further includes a vasodilator. Typically, the vasodilator includes magnesium; however, the vasodilator, for purposes of the subject disclosure, may include other vasodilators in place of or in addition to magnesium, in place of or in addition to those including magnesium, or may include only magnesium or only magnesium-containing compounds. Vasodilators are known in the art for use in preventing hearing loss. Vasodilators including magnesium prevent decreases in cochlear blood flow and oxygenation via biochemical mechanisms involving changes in calcium concentration and prostaglandins. Deficient cochlear blood flow and lack of oxygenation are factors that contribute to hearing loss by causing cell death in sensitive hair cells within a cochlea of the ear. Vasodilators including magnesium have also been found to improve the efficacy of immunosuppressant therapy or carbogen inhalation therapy in recovery from sudden hearing loss. Furthermore, it has been found that magnesium deficiency leads to increased calcium channel permeability and greater influx of calcium into cochlear hair cells, increased glutamate release, and auditory nerve excitotoxicity, each of which play a role in health of the inner ear. Although the vasodilators are known in the art for treating hearing loss, the vasodilators, especially those including magnesium, exhibit an unexpected additive effect when combined with the biologically effective amounts of the at least one scavenger of singlet oxygen, the donor antioxidant, and the third antioxidant, especially when the at least one scavenger of singlet oxygen is vitamin A, the donor antioxidant is vitamin E, and the third antioxidant is vitamin C for purposes of treating noise-induced hearing loss. Similar excellent effectiveness has also been found when the composition is used to treat side effects of antibiotic treatment including antibiotic-induced hearing loss. The additive effect referred to above is greater than not only the most efficacious of the components for treating hearing loss, but typically greater than the sum of the effects of each of the components for treating hearing loss. While vasodilators other than those including magnesium are envisioned for purposes of the present disclosure, additive effects are not observed with all vasodilators. For example, betahistine, which is another known vasodilator, does not exhibit an additive effect as is evident from FIG. 1. Specific effects of the composition of the subject disclosure on treating noise-induced hearing loss and side effects of antibiotic treatment are described in further detail below.

The vasodilator including magnesium typically includes a magnesium salt or magnesium salt complex and, more specifically, magnesium sulfate or magnesium citrate. Other vasodilators including magnesium that may be suitable for purposes of the subject disclosure include: magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, magnesium stearate, and magnesium sulfate. Other representative salts include but are not limited to; hydrobromide, hydrochloride, bisulfate, nitrate, arginate, ascorbate, oxalate, valerate, oleate, palmitate, laurate, borate, benzoate, phosphate, tosylate, maleate, fumarate, succinate, taurate, tartrate, naphthylate, mesylate, glucoheptonate, lactobionate and laurylsulphonate salts.

Typically, the vasodilator is present in the composition in an amount of at least 50 mg. For example, when the vasodilator is magnesium, the magnesium is typically present in an amount of from 50 to 450 mg, most typically from 100 to 350 mg. As with vitamins A, C, and E, specific amounts of the vasodilator present in the composition may be dependent on the body weight of the mammal. In one specific example, the amount of the vasodilator including magnesium present in the composition is about 4.46 mg/kg body weight. Thus, for an average human weighing about 70 kg, the amount of the vasodilator including magnesium present in the composition may be about 312 mg. In another example, the amount of the vasodilator including magnesium present in the composition is about 2.14 mg/kg body weight. Thus, for an average human weighing about 70 kg, the amount of the vasodilator including magnesium present in the composition may be about 150 mg.

Non-limiting examples of amounts of the typical components included in the composition, along with more and most typical amounts, are summarized in Table 1 below.

TABLE 1

| Component | | Amount | More Typical Amount | Most Typical Amount | Typical Dosage, mg/kg body weight |
|---|---|---|---|---|---|
| Vitamin A | | ≥830 IU | 830-10,000 IU | 2100-8,000 IU | 0.0178 mg/kg |
| | Vitamin A As beta-carotene | ≥830 IU | 830-50,000 IU | 2,000-30,000 IU | 0.257 mg/kg |
| Vitamin C | | ≥4,000 IU | 4,000-60,000 IU | 8,000-20,000 IU | 7.14 mg/kg |
| Vitamin E | | ≥75 IU | 75-2000 IU | 150-800 IU | 3.8 mg/kg (synthetic) |
| Magnesium | | ≥50 mg | 50-450 mg | 100-350 mg | 4.46 mg/kg |

With respect to Table 1, the amounts specified for the antioxidants and the vasodilator correlate, in terms of biological effectiveness, to amounts used for humans. Furthermore, it is to be appreciated that the biologically effective amounts of the antioxidants and vasodilator may be lower within the above ranges for children than for the average human, based on lower US recommended daily allowances and maximum intake levels for children. This is evident based on the typical dosages in Table 1 based on mg/kg.

Other non-limiting examples of amounts of the typical components included in the composition, along with more and most typical amounts, are summarized in Table 2 below.

TABLE 2

| Component | | Amount | More Typical Amount | Most Typical Amount | Typical Dosage, mg/kg body weight |
|---|---|---|---|---|---|
| Vitamin A | | ≥830 IU | 830-120,000 IU | 2,100-70,000 IU | — |
| | Vitamin A As Retinol | ≥830 IU | 830-50,000 IU | 2,100-5,900 IU | 0.0178 mg/kg |
| | Vitamin A As beta-carotene | ≥10,000 IU | 10,000-120,000 IU | 25,000-70,000 IU | 0.214 mg/kg |
| Vitamin C | | ≥4,000 IU | 6,000-40,000 IU | 8,000-20,000 IU | 7.14 mg/kg |
| Vitamin E | | ≥75 IU | 75-1,500 IU | 150-800 IU | 2.6 mg/kg |
| Magnesium | | ≥50 mg | 50-450 mg | 100-350 mg | 2.14 mg/kg |

With respect to Table 2, the amounts specified for the antioxidants and the vasodilator correlate, in terms of biological effectiveness, to amounts used in animal studies on guinea pigs. Furthermore, it is to be appreciated that the biologically effective amounts of the antioxidants and vasodilator may be lower within the above ranges for children than for the average human, based on lower U.S. recommended daily allowances and maximum intake levels for children. This is evident based on the typical dosages in Table 2 based on mg/kg.

In addition to the antioxidants and vasodilator, other components may also be present in the composition for treating hearing loss, as well as for treating the side effects of the antibiotic treatment. For example, in one embodiment, the composition further includes a withanolide. Withanolides have been suggested for use in anti-inflammatory, anti-tumor, cytotoxic, and immunological applications. One example of a specific withanolide that may be included in the composition of the subject disclosure is the withanolide extracted from day 111y plants. The extract is a powerful natural antioxidant which may be effective in preventing cell death in the inner ear by interrupting the cell-death pathway initiated by deafferentation of the auditory nerve. When included in the composition, the withanolide may be present in an amount of at least 10 ppm, more typically from 10 to 1000 ppm. Additional components, besides withanolides, can also be included. Typically, the composition is free of components that interfere with the biological mechanisms through which the at least one scavenger of singlet oxygen, the donor antioxidant, the third antioxidant, and the vasodilator function. The composition is also typically free of additional components that could degrade or neutralize the at least one scavenger of singlet oxygen, the donor antioxidant, the third antioxidant, and the vasodilator function when mixed therewith prior to internally administering the composition to the mammal. Those of skill in the art can readily identify such components in view of the mechanisms by which the individual components in the composition function as set forth above (e.g., components that cause vasoconstriction, various oxidizing agents, etc.).

It is also to be appreciated that, even if additional components are present in the composition that could interfere with the mechanisms by which the at least one scavenger of singlet oxygen, the donor antioxidant, the third antioxidant, and the vasodilator function, the composition described above is still effective for purposes of treating side effects of the antibiotic treatment. As one example, and as described in further detail below, the composition including the at least one scavenger of singlet oxygen, the donor antioxidant, the third antioxidant, and the vasodilator is still effective for treating hearing loss and other side effects of antibiotic treatment when administered in conjunction with aminoglycoside antibiotics (as made clear with reference to FIG. 5). This is true even though aminoglycoside antibiotics, themselves, are responsible for causing hearing loss and other side effects such as kidney damage and loss of balance through free radical formation.

In view of the fact that components as detrimental as aminoglycosides can be administered in conjunction with the composition described above, it is clear that additional components that are less detrimental to the specific mechanisms by which the at least one scavenger of singlet oxygen, the donor antioxidant, the third antioxidant, and the vasodilator function can also be present in the composition with an expectation that the composition maintains effectiveness for purposes of treating side effects of antibiotic treatment such as antibiotic-induced hearing loss. Examples of some additional components that may be included in the composition include, but are not limited to, excipients, flavoring agents, fillers, binders, and additional vitamins or minerals not specifically mentioned herein.

As alluded to above, the method of treating hearing loss and the method of treating side effects from antibiotic treatment of the instant disclosure includes the step of internally administering the composition of the subject disclosure to a mammal. More specifically, the instant method is for treating side effects of antibiotic treatment such as antibiotic-induced hearing loss, kidney damage, and loss of balance. The examples of the composition may be orally administered to the mammal, such as in the form of a tablet, liquid, gel, etc. Alternatively, the composition may be intravenously administered to the mammal through an IV or an injection of the composition. When specifically used to treat antibiotic-induced hearing loss, the composition may also be locally administered via the round window membrane of the cochlea. As a specific example, the vitamins A, C, and E, the vasodilator including magnesium, and the optional components may be first combined to form the composition, with the composition then administered to the mammal. Alternatively, the vitamins A, C, and E, the vasodilator including magnesium, and the other optional components may be separately administered, in which case the composition forms within the mammal.

For purposes of the subject disclosure, hearing loss may be objectively measured in terms of differences in threshold shift, or through measurement of a percentage of hair cell loss. In guinea pig studies, hearing loss and the efficacy of the composition for treating antibiotic-induced hearing loss may be measured as an average difference in threshold shift from baseline threshold sensitivity at 4, 8, and 16 kHz, as compared to an untreated control, after exposure to 120 decibel SPL Octave Band Noise centered at 4 kHz for five hours. Larger differences in threshold shift correlate to less hearing loss and greater efficacy of the composition for treating the antibiotic-induced hearing loss.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell.

In one embodiment, the composition of the present disclosure is administered to the mammal within three days of trauma to the inner ear of the mammal in order to alleviate permanent threshold shift. It is to be appreciated that by administering the composition within three days of trauma, treatment prior to trauma is also contemplated through the method of the present disclosure. Data from animal studies indicate that temporary threshold shift measured 24 hours post-trauma is well-correlated with permanent threshold shift. Given the relationship between temporary threshold shift and permanent threshold shift, it is clinically beneficial to reduce temporary threshold shift. As such, the composition is typically administered within one day of trauma to the inner ear of the mammal. Even so, it is expected that treatment within three days with the composition of the present disclosure is substantially as effective in minimizing permanent threshold shift as treatment within one day.

Treatment within three days is most appropriate when the mammal has sustained trauma to the inner ear through unexpected loud noise or other trauma. Ideally, the composition is administered to the mammal prior to trauma to the inner ear. Treatment prior to trauma is most feasible when the mammal is preparing for sustaining trauma to the inner ear. For example, the composition may be administered prior to restoration surgery performed on the inner ear. As another example, if a person will be firing a weapon or attending an event such as a rock concert, the person may begin treatment prior to sustaining the trauma to the inner ear to attain the best results.

After initial administration of the composition, the composition is typically administered to the mammal each day for at least five days following the trauma to the inner ear of the mammal. Although excellent results have been achieved through such treatment, it is to be appreciated that other treatment regimens may also prove efficacious for purposes of the present disclosure.

For the method of treating side effects of antibiotic treatment, the composition is internally administered to the mammal in conjunction with administration of the antibiotic. In this regard, the method also includes the step of internally administering the antibiotic, which antibiotic is capable of inducing hearing loss in the mammal. It is to be appreciated that, even though the antibiotic with which the composition is administered is capable of inducing hearing loss, the method of the instant disclosure is not strictly limited to treatment of hearing loss that is induced by the antibiotics. More specifically, the method of the instant disclosure proscribes the step of administering the subject composition in conjunction with administration of the antibiotic for any purpose including for treating any side effect of the antibiotics including not only antibiotic-induced hearing loss, but also kidney damage, loss of balance, among other side effects.

Specific non-limiting examples of antibiotics that are capable of inducing hearing loss in mammals include aminoglycoside antibiotics such as amikacin, arbekacin, gentamicin, kanamycin, neomycin, netilmicin, paromomycin, rhodostreptomycin, streptomycin, tobramycin, and apramycin; and glycopeptide antibiotics such as vancomycin, teicoplanin, telavancin, bleomycin, ramoplanin, and decaplanin. The treatment is particularly effective against aminoglycoside-induced side effects. In one specific embodiment, the antibiotic is gentamicin, which is commonly used in developing countries due to low cost and effectiveness against certain drug-resistant diseases.

The dosages of the antibiotic that are administered to the mammal may vary within the medically-accepted ranges for therapeutic treatment, as may the number of days over which the antibiotic is administered. The antibiotic is typically administered daily. For purposes of objectively establishing the effectiveness of the treatment described herein, a dosage of 140 g of gentamicin was administered to guinea pigs for a period of 16 days. However, it is to be appreciated that the specific dosages and days over which the antibiotic is administered are not material for purposes of establishing the viability of the treatment described herein so long as the composition described herein is administered in conjunction with administration of the antibiotic (although the effectiveness of the treatment described herein may vary based upon dosages and days over which the antibiotics are administered).

For purposes of the instant disclosure, administration of the composition described herein "in conjunction with" administration of the antibiotic refers to a connection in the administration of the composition and the antibiotic during the course of antibiotic treatment. To maximize effectiveness of the treatment described herein, it is desirable to establish stable serum levels of the at least one scavenger of singlet oxygen, the donor antioxidant, the third antioxidant, and the vasodilator at the time that the antibiotics reach serum levels within the mammal that cause material side effects such as hearing loss. Typically, the composition is internally administered to the mammal no longer than three days after administration of a first dosage of the antibiotic, which is sufficient to achieve the stable serum levels of the at least one scavenger of singlet oxygen, the donor antioxidant, the third antioxidant, and the vasodilator before the antibiotics begin to materially cause the side effects such as hearing loss. In one embodiment, the composition is internally administered prior to administration of the first dosage of the antibiotic. In this embodiment, the composition may be administered at least five days, alternatively at least ten days, prior to administration of the first dosage of the antibiotic for purposes of maximizing the effectiveness of the treatment for side effects of antibiotic treatment described herein.

Once administration of the composition has begun, the composition is typically administered each day the antibiotic is administered to maintain adequate serum levels of the at least one scavenger of singlet oxygen, the donor antioxidant, the third antioxidant, and the vasodilator. Additionally, the composition is typically administered for at least 1, 2, 3, 4, 5, 6, 7, 8, 9, 10, 11, 12, 13, 14, 15, 16, 17, 18, 19, 20, or 21 days following cessation of administration of the antibiotic.

This is typically performed for purposes of ensuring that adequate serum levels of the at least one scavenger of singlet oxygen, the donor antioxidant, the third antioxidant, and the vasodilator are maintained until the serum levels of the antibiotic decrease, and typically until all of the additional free radicals formed secondary to the antibiotic treatment are eliminated.

As described in further detail in the Examples section below, an average difference in threshold shift in mammals from baseline threshold sensitivity at 4, 8, and 16 kHz, as compared to an untreated control, is at least 25 decibels after exposure to 120 decibel SPL Octave Band Noise centered at 4 kHz for five hours. More specifically, the threshold shift in mammals treated with the composition of the present disclosure is expected to be at least 25 decibels lower than the threshold shift in mammals that are treated with a control saline solution. To obtain those results, the composition is orally administered one hour prior to exposure to the noise and administered again each day for five days subsequent to the exposure to the noise. The threshold shift is measured 10 days after exposure to the noise using auditory brainstem response (ABR) testing. Similar results would be anticipated using other alternative measures of auditory or sensory cell function, such as psychophysical tests or otoacoustic emission measures. While effectiveness of treatment in accordance with the method of the instant disclosure is objectively proven herein through measurement of shifts in threshold hearing loss, it is to be appreciated that the method is not strictly limited to treatment of hearing loss alone and broadly encompasses administration of the subject composition in conjunction with administration of the particular antibiotics described herein.

Figure 5:
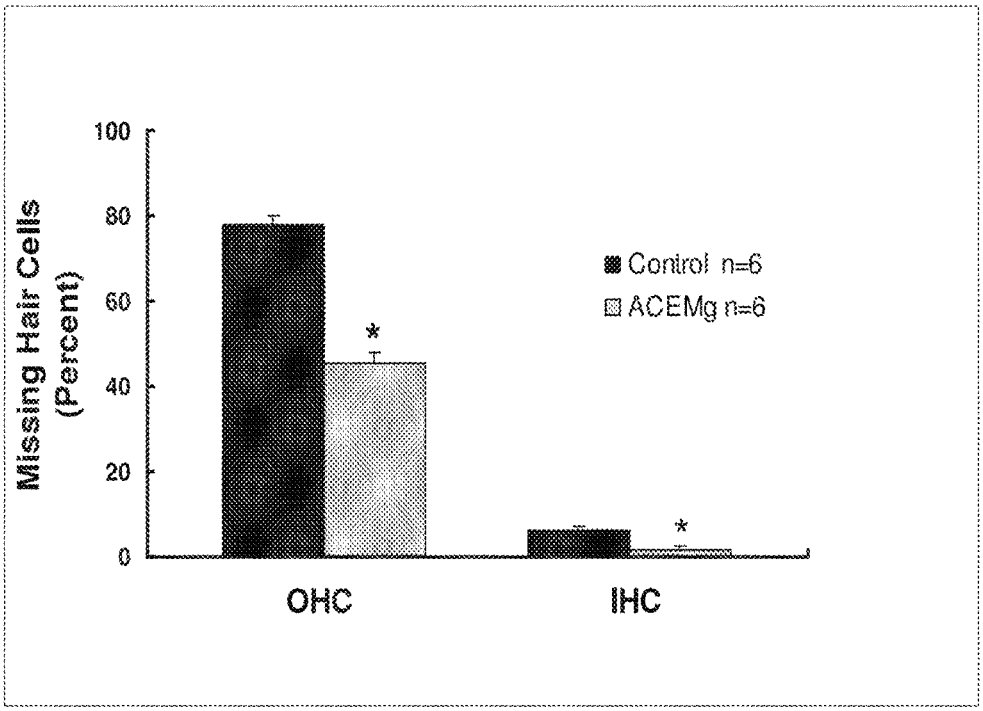
FIG. 5 is a graph showing the effect of treatment of side effects of antibiotic treatment, as a measurement of percentage of outer hair cells and inner hair cells lost in guinea pigs, when the composition including vitamins A, C, and E and magnesium is administered in conjunction with administration of aminoglycoside antibiotics in accordance with the method of the subject disclosure versus a control in which aminoglycoside antibiotic is administered alone.

In addition, outer hair cell loss and inner hair cell loss is measured both in the whole cochlea and in a trauma region of the cochlea. After treatment according to the method of the present disclosure, outer hair cell loss in the whole cochlea is less than 10%, and inner hair cell loss in the whole cochlea is less than 5%. Outer cell hair loss in the trauma region is less than 20%, while inner hair cell loss in the trauma region is less than 10%. For the method of treatment in accordance with the present disclosure, as shown in FIG. 5, outer hair cell loss in the whole cochlea is less than 50%, while inner hair cell loss in the whole cochlea is less than 5%. To obtain those results, the composition is orally administered to guinea pigs for 10 to 16 days prior to first administration of the antibiotic, and the composition and antibiotic are administered again each day for forty days. The guinea pigs are then euthanized and the hair cells counted. Conversely, when the antibiotic is administered for forty days without administering the composition described herein in conjunction with the antibiotic, outer hair cell loss approaches 80%, while inner hair cell loss is about 8%.

The following examples, as presented herein, are intended to illustrate and not limit the disclosure.

REFERENCE EXAMPLE

A method of treating noise-induced hearing loss is performed on guinea pigs (NIH outbred strain, 250-350 grams) as a reference example for the instant application. The guinea pigs are used due to their extensive use in auditory research, including studies on noise-induced hearing loss, and because they provide a model similar to humans in terms of development. Six guinea pigs are subject to treatment with the composition of the present disclosure. In order to determine efficacy of the composition of the present disclosure in treating hearing loss, baseline threshold sensitivity of the guinea pigs is measured binaurally using auditory brainstem response testing at 4, 8, and 16 kHz. The guinea pigs are then treated with vitamins A, C, E, and magnesium (referred to in FIGS. 2-7 as "ACEMg") in the amounts shown in Table 3. The amounts shown in Table 3 are approximately 3 times expected human doses based on more rapid metabolism of guinea pigs relative to humans.

TABLE 3

| Component | Parts by Weight |
|---|---|
| Vitamin A (beta-carotene) | 2.1 mg/kg p.o. |
| Vitamin C (Ascorbic acid) | 71.4 mg/kg s.c |
| Vitamin E (Trolox ®) | 26 mg/kg s.c. |
| Magnesium (MgSO4) | 2.85 mmol/kg s.c. |

One hour later, the guinea pigs are exposed to 120-dB SPL Octave Band Noise centered at 4 kHz for 5 hours to cause trauma to inner ears of the guinea pigs. The noise is sufficient to cause permanent threshold shift, i.e., permanent hearing loss. The composition of the present disclosure is administered immediately post-exposure to the noise, and again each day for 5 days after the trauma. Ten days after the trauma, auditory sensitivity is measured using ABR. For ABR testing, the guinea pigs are anesthetized with 40 mg/kg ketamine and 10 mg/kg xylazine and placed on a warm heating pad in a sound attenuated chamber. ABR thresholds are determined at 4, 8 and 16 kHz frequencies. To test for the ABR thresholds, tone bursts 10 ms in duration (0.5 ms rise/fall) are presented at a rate of 17/sec. Up to 1024 responses are collected and averaged for each signal frequency to provide a measure of threshold shift at each frequency. Estimates of permanent hearing loss, shown in FIG. 2 in terms of threshold shift in decibels, are calculated as average threshold shift across ears and across frequencies.

Figure 3:
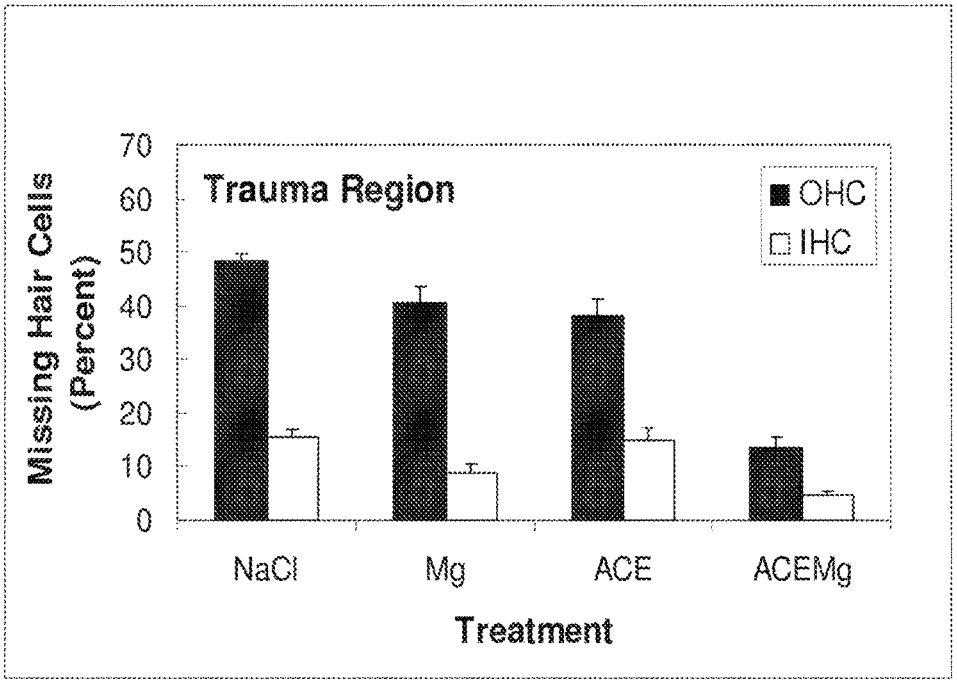
FIG. 3 is a graph showing the effect of treatment in accordance with the instant disclosure using the composition of the subject disclosure and treatments using Comparative Examples of compositions of FIG. 2 on an amount of missing hair cells in the region of the cochlea that is most damaged after the noise exposure specified above for FIG. 2.
Figure 4:
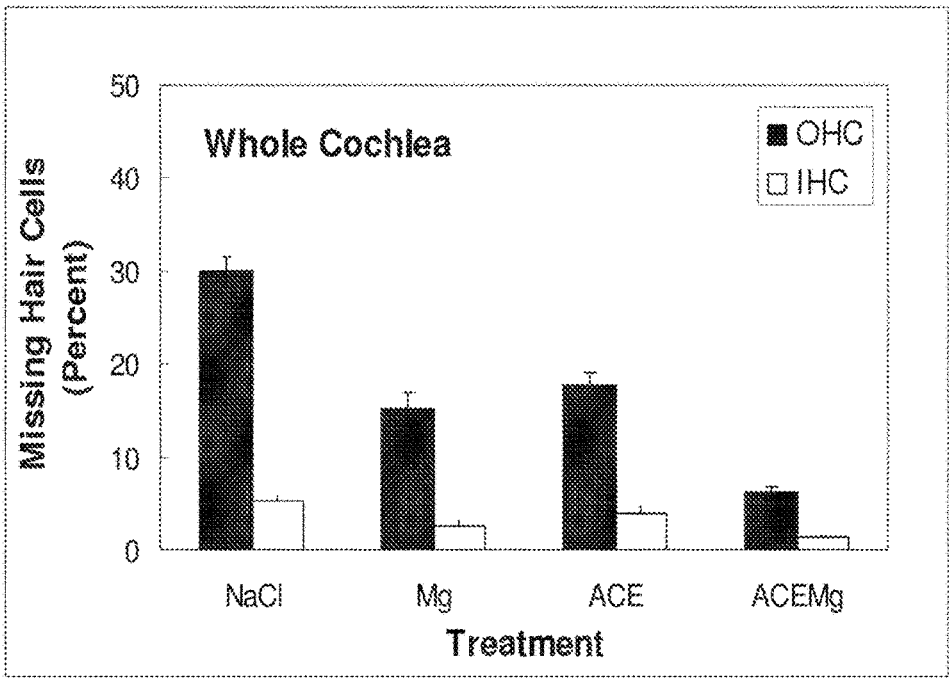
FIG. 4 is a graph showing the effect of treatment in accordance with the instant disclosure using the composition including vitamins A, C, and E and magnesium and treatments using Comparative Examples of compositions of FIG. 2 on an amount of missing hair cells in the whole cochlea after the noise exposure specified above for FIG. 2.

After ABR testing, the guinea pigs are deeply anesthetized and decapitated. Temporal bones are quickly removed, dissected open and fixed with 4% paraformaldehyde. The following day, an otic capsule, lateral wall, and tectorial membrane are removed, and a bony modiolus is carefully detached. Organ of Corti tissue, attached to the modiolus, is permeabilized with 0.3% Triton-X and incubated with rhodamine phalloidin diluted 1:100 in phosphate buffered saline (30 min). After washing the tissues, individual turns from the organ of Corti are dissected, mounted on microscope slides, and examined and photographed using a Leica DMRB epiflourescence microscope. Hair cell counts are conducted, and cytocochleograms are prepared as known in the art. Referring to FIGS. 3 and 4, percentages of missing inner hair cells (IHC) and outer hair cells (OHC) are determined based on the hair cell counts.

Example 1

The method of treating side effects of antibiotic treatment with the composition of the present disclosure is again performed on guinea pigs (normal hearing, male, pigmented). Six guinea pigs are subject to antibiotic administration and treatment with the composition of the present disclosure. The guinea pigs were fed with a chow containing the composition including beta-carotene, vitamin C, vitamin E, and magnesium in the amounts shown in Table 3 for 10 days prior to administration of a first dosage of gentamicin antibiotic, and were fed the same chow every day for 41 days. The guinea pigs consumed a normal diet sufficient to allow them to gain weight. Gentamicin was administered to the guinea pigs subcutaneously once a day for 16 consecutive days after administration of the first dosage of the gentamicin. Body weights were monitored and the guinea pigs were observed for clinical signs of systemic toxicity. Guinea pigs losing weight were treated with subcutaneous saline and the chow was administered orally as gruel. Fourteen days following cessation of antibiotic treatment, the guinea pigs were euthanized, left cochleae harvested, and quantitative sensory hair cell assessments were performed. The amounts shown in Table 4 are approximately 10 times expected human doses based on more rapid metabolism of guinea pigs relative to humans.

TABLE 4

| Component | Parts by Weight |
|---|---|
| Antibiotic (Gentamicin) | 140 mg/kg |
| Vitamin A (beta-carotene) | 1 g/kg p.o. |
| Vitamin C (Ascorbic acid) | 20 g/kg s.c |
| Vitamin E (Trolox ®) | 7 g/kg s.c. |
| Magnesium (MgSO4) | 30 g/kg s.c. |

Comparative Example 1

Figure 2:
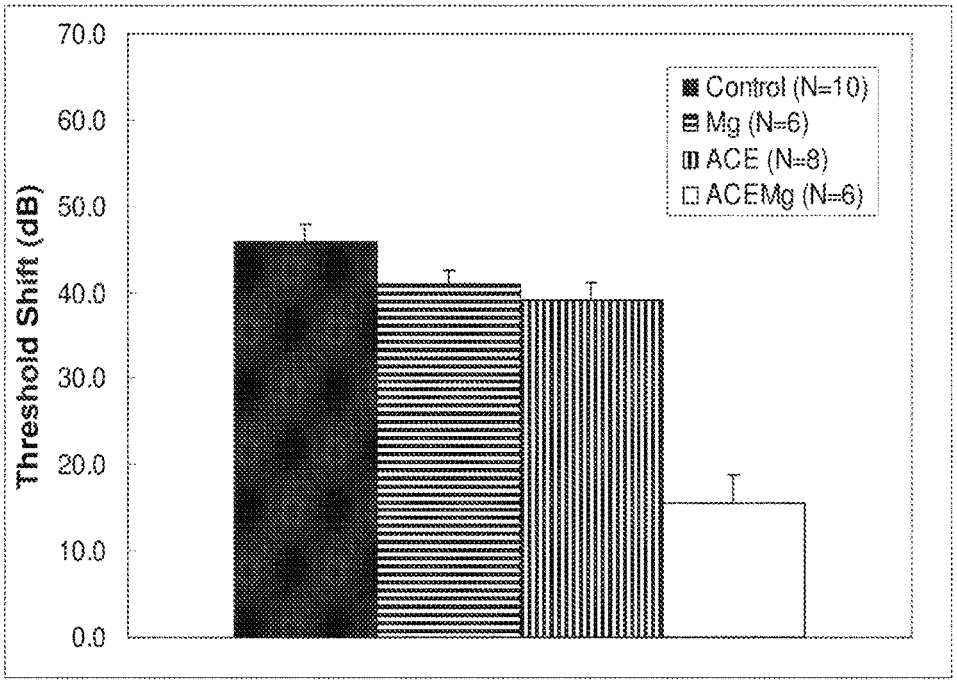
FIG. 2 is a graph showing the effect of treatment in accordance with the instant disclosure using a composition including vitamins A, C, and E and magnesium, and comparative examples of treatments using compositions that include only some of those components, on average reduction of a threshold shift in guinea pigs from baseline threshold sensitivity at 4, 8, and 16 kHz after exposure to 120 decibel SPL Octave Band Noise centered at 4 kHz for five hours.

Guinea pigs are treated with other compositions in order to compare the efficacy of the composition of the present disclosure with the other compositions. For example, guinea pigs are separately treated in the same way as specified above in the Example with the following compositions: a saline (NaCl) composition as a control, a composition including only magnesium sulfate (2.85 mmol/kg), or a composition including only vitamins A (2.1 mg/kg beta-carotene), C (71.4 mg/kg ascorbic acid), and E (26 mg/kg Trolox®) ("ACE"). The guinea pigs are subjected to the same ABR testing, and the components of the ear are dissected, as described above in the Example to provide information on threshold shift and hair cell loss. Threshold shift and hair cell loss resulting from treatment with the other compositions are shown in FIGS. 2-4.

Comparative Example 2

Guinea pigs are treated with a composition of vitamin E alone, betahistine alone, or a combination of betahistine and vitamin E to determine if results similar to those achieved with the composition of the present disclosure including magnesium can be achieved by substituting betahistine for the magnesium. The results of treatment with vitamin E, betahistine, or combination of vitamin E and betahistine are shown in FIG. 1. In one comparative example, guinea pigs are treated once daily with 100 mg/kg vitamin E (Trolox®), 30 mg/kg Betahistine, or a combination of 100 mg/kg Trolox® and 30 mg/kg Betahistine. Five guinea pigs are treated with each of the different compositions. In another comparative example, four guinea pigs are separately treated with 50 mg/kg Trolox® twice daily, 18 mg/kg Betahistine (one dose immediately pre-noise exposure), or a combination of 50 mg/kg vitamin E (Trolox®) and 18 mg/kg Betahistine (N=4 animals per group). Control data are from 18 animals treated with saline delivered either IP (N=11) or IV (N=7). The guinea pigs are subjected to ABR testing, and the components of the ear are dissected, both as described above in the Example, to provide information on threshold shift and hair cell loss.

Comparative Example 3

Six guinea pigs are subject to antibiotic administration in the absence of treatment with the composition of the present disclosure. Gentamicin was administered to the guinea pigs subcutaneously in an amount of 140 mg/kg body weight once a day for 16 consecutive days after administration of the first dosage of the gentamicin. Body weights were monitored and the guinea pigs were observed for clinical signs of systemic toxicity. Guinea pigs losing weight were treated with subcutaneous saline. The weight gain of the six guinea pigs, which were on a non-supplemented diet, was statistically the same as the guinea pigs in Example 1. Fourteen days following cessation of antibiotic treatment, the guinea pigs were euthanized, left cochleae harvested, and quantitative sensory hair cell assessments were performed.

Comparative Example 4

Figure 6:
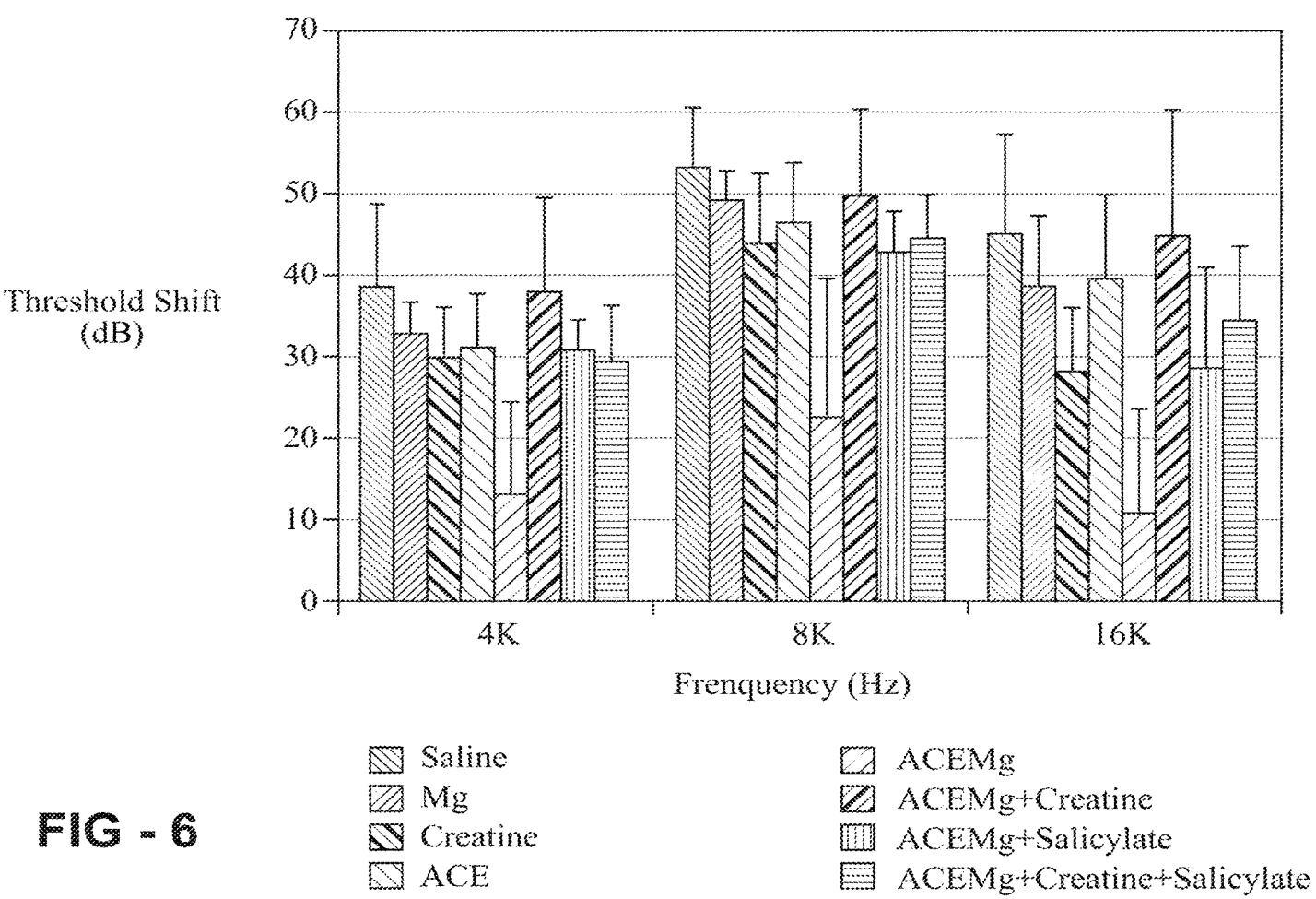
FIG. 6 is a graph showing a mean threshold shift of hearing loss in guinea pigs treated with an inventive composition consisting essentially of vitamin A, vitamin C, vitamin E, and magnesium, and treated with comparative compositions including i) saline, ii) magnesium, iii) vitamins A, C, and E, iv) creatine, v) vitamin A, vitamin C, vitamin E, magnesium, and creatine, and vi) vitamin A, vitamin C, vitamin E, magnesium, creatine, and salicylate, where the mean threshold shift is measured at baseline threshold sensitivities of 4, 8, and 16 kHz after exposure to 120 decibel SPL Octave Band Noise centered at 4 kHz for five hours.
Figure 7:
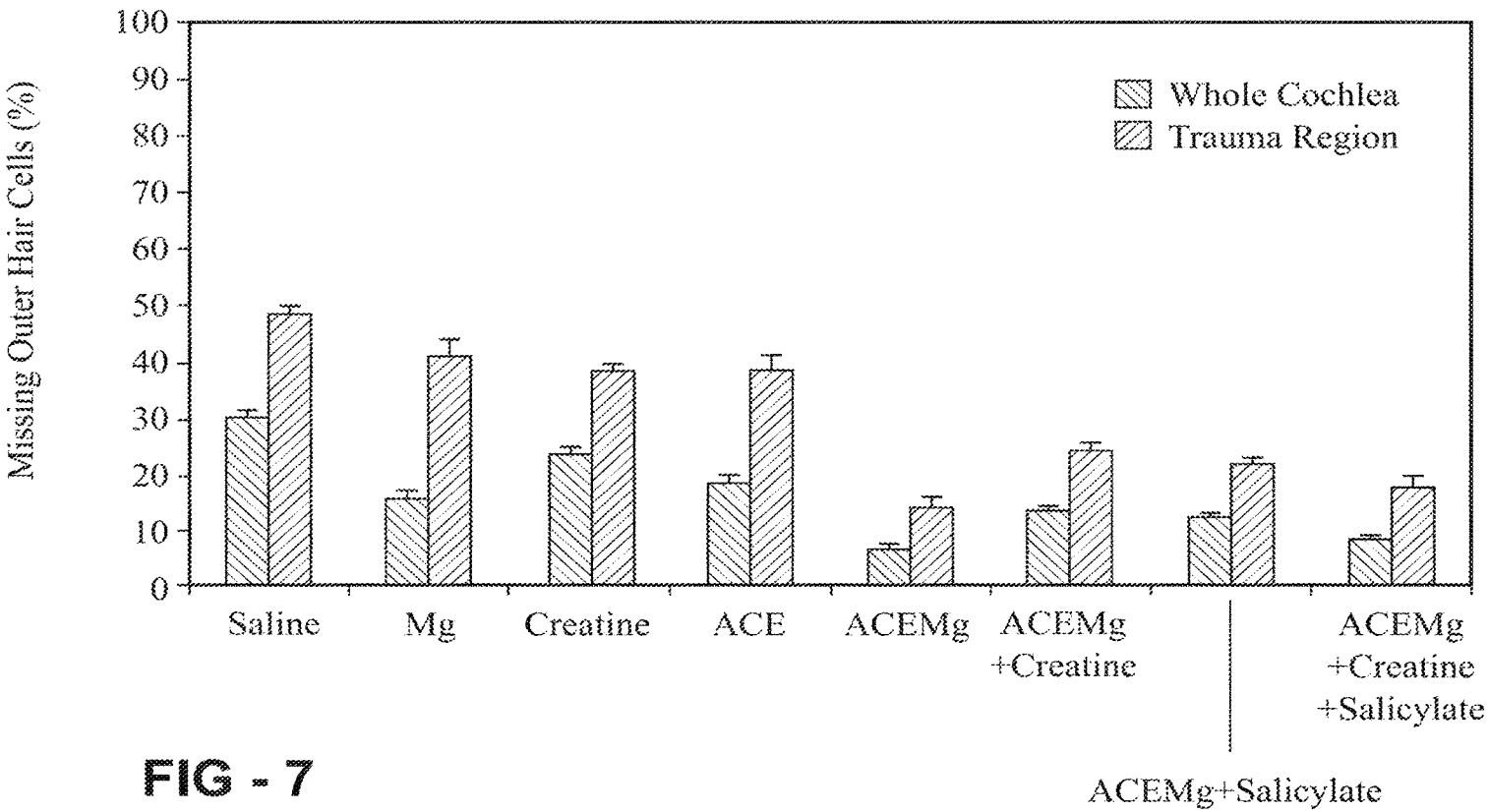
FIG. 7 is a graph showing side effects of treatment of the guinea pigs by an inventive composition consisting essentially of vitamin A, vitamin C, vitamin E, and magnesium, and by comparative compositions including i) saline, ii) magnesium, iii) vitamins A, C, and E, iv) creatine, v) vitamin A, vitamin C, vitamin E, magnesium, and creatine, and vi) vitamin A, vitamin C, vitamin E, magnesium, creatine, and salicylate, the side effects of the treatment being a measurement of percentage of outer hair cells lost in the guinea pig in the whole cochlea and in the trauma region after the noise exposure.

Eight groups of guinea pigs (where the number of guinea pigs ranges from 5 guinea pigs to 10 guinea pigs per group) are respectively treated with other compositions to compare the efficacy of the "ACEMg" composition of the present disclosure with the other compositions. For example, the guinea pigs are separately treated in the same way as specified above in the Example with the following compositions: a saline (NaCl) composition as a control, a composition including only $MgSO_4$ (2.85 mmol/kg), a composition including creatine (3% monohydrate diet), a composition including only vitamins A (2.1 mg/kg beta-carotene), C (71.4 mg/kg ascorbic acid), and E (26 mg/kg Trolox®) ("ACE"), a composition including "ACEMg" (2.1 mg/kg of vitamin A, 71.4 mg/kg of vitamin C, 26 mg/kg of vitamin E, and 2.85 mmol/kg of $MgSO_4$) and creatine (3% monohydrate diet), and a composition including "ACEMg" (2.1 mg/kg of vitamin A, 71.4 mg/kg of vitamin C, 26 mg/kg of vitamin E, and 2.85 mmol/kg of $MgSO_4$), creatine (3% monohydrate diet), and salicylate (75 mg/kg). The eight groups of guinea pigs are exposed to the same ABR testing, and the components of the ear are dissected as previously described in the Example to provide information on threshold shift and outer hair cell loss. The threshold shift of hearing loss and the outer hair cell loss resulting from treatment with the "ACEMg" composition and the other compositions tested are shown in FIGS. 6 and 7, respectively.

Results

Referring to FIGS. 2-4, the effect in treating hearing loss with composition of the present disclosure including vitamins A, C, E, and magnesium is clearly greater than that associated with the effectiveness of a composition including only magnesium or only vitamins A, C, and E. More specifically, treatment with the composition of the present disclosure results in threshold shift of less than 20 decibels, as averaged across all frequencies, while treatment with a control saline solution results in a threshold shift of about 45. As such, a difference in threshold shift between treatment with the composition of the present disclosure and treatment with the control of saline solution is over 25 decibels. Furthermore, the difference in threshold shift between the composition of the present disclosure and the control saline solution is greater than the sum of differences in threshold shifts for magnesium or vitamins A, C, and E alone and the control saline solution. Specifically, the sum of the differences in threshold shifts for magnesium and vitamins A, C, and E alone is about 12 decibels. It is to be understood that the decibel scale is a logarithmic scale. As such, a difference in the threshold shift of hearing loss of 12 decibels for the composition consisting essentially of magnesium and vitamins A, C, and E and Mg represents a fourfold difference in efficacy compared to the other compositions tested. This result demonstrates a highly synergistic interaction among the individual components of the composition consisting essentially of magnesium and vitamins A, C, and E. Furthermore, the difference in the threshold shift of hearing loss of about 45 decibels for the composition including saline and the difference in the threshold shift of hearing loss of about 20 decibels for the composition including vitamins A, C, and E is similar to the difference between a moderate handicap and a severe handicap.

Consistent with the reduction in noise-induced hearing loss, hair cell counts revealed significantly reduced sensory cell death with Mg or A, C, and E, with the greatest protection observed after treatment with vitamins A, C, E, and magnesium. More specifically, less than 10% of outer hair cells and less than 5% of inner hair cells in the whole cochlea are missing after treatment with the composition of the present disclosure including Mg and vitamins A, C, and E. In the trauma region, less than 20% of outer hair cells and less than 10% of inner hair cells in the whole cochlea are missing after treatment with the composition of the present disclosure including Mg and vitamins A, C, and E. As shown by FIGS. 3 and 4, the reduction in percentage of missing hair cells after treatment with the composition of the present disclosure is more than the sum of the reductions in missing hair cells observed when magnesium or vitamins A, C, and E are used alone as compared to the percentage of hair cell loss when saline is used.

Furthermore, as shown in FIG. 1, the Comparative Examples in which vitamin E, betahistine, or a combination of vitamin E and betahistine are used clearly do not exhibit the same additive effect that is observed when magnesium is used as the vasodilator in combination with the vitamins to treat noise-induced hearing loss. More specifically, saline treated control animals (white bars) show the greatest hearing loss 10 days post noise. Animals treated with Vitamin E (Trolox®: 100 mg/kg once daily or 50 mg/kg twice daily, diagonal lined bars) have less permanent hearing loss than control animals. Animals treated with the vasodilator betahistine (30 mg/kg, once daily, vertical striped bars; or one 18 mg/kg dose pre-noise, horizontal striped bars) show approximately the same amount of protection as those treated with vitamin E. Animals treated with a combination of vitamin E and betahistine (50 mg/kg Trolox® twice daily+18 mg/kg betahistine twice daily, or 100 mg/kg Trolox® once/daily+30 mg/kg betahistine once/daily; see dark bars with white diagonal hatch) do not have any additive protection against noise-induced hearing loss beyond that of either single agent alone. As such, not all vasodilators are as effective as magnesium in combination with the vitamins.

In terms of comparison of the method of treating side effects of antibiotic treatment in terms of measurement of antibiotic-induced hearing loss as shown in Example 1 with Comparative Example 3, dramatic cell death of outer hair cells was observed through the treatment of Comparative Example 3 due to the ototoxic effects of the gentamicin antibiotic. Referring to FIG. 5, it can be seen that statistically significant reduction in antibiotic-induced hearing loss (as gauged by quantitative sensory hair cell assessments) through the treatment described in Example 1 versus the treatment described in Comparative Example 3. In particular, both outer and inner hair cells are protected through the treatment in accordance with Example 1.

Referring now to FIGS. 6 and 7, the effect in treating hearing loss with the composition of the present disclosure which consists essentially of vitamin A, vitamin C, vitamin E, and a vasodilator comprising magnesium ("ACEMg") is clearly superior to the effect of treating hearing loss with the other compositions tested. As shown in FIG. 6, treatment with the composition consisting essentially of "ACEMg" results in a threshold shift of hearing loss of less than 20 decibels, as averaged across all frequencies. Treatment with a control saline solution results in a threshold shift of 45 decibels, as averaged across all frequencies. Treatment with the composition including magnesium results in a threshold shift of about 41 decibels, as averaged across all frequencies, while treatment with the composition including "ACE" results in a threshold shift of about 39 decibels, as averaged across all frequencies. Noting that an average threshold shift that is high (e.g., about 25 decibels or higher) is undesirable and considered to be a clinically significant hearing handicap, the average threshold shift of the composition consisting essentially of "ACEMg" is low (e.g., about 15 decibels). The low average threshold shift of the composition consisting essentially of "ACEMg" is significantly less than the average threshold shift of any of the other compositions (each producing threshold shifts of hearing loss that is well over 25 decibels). This result shows that the composition consisting essentially of "ACEMg" performs better than any of the other compositions tested in terms of treating hearing loss.

As shown in FIG. 7, outer hair cell counts reveal reduced sensory cell death in both the whole cochlea and in the trauma region, compared to the saline control, with i) the guinea pig treated with a composition including magnesium and ii) the guinea pig treated with a composition including "ACE". However, the best results were obtained utilizing a composition consisting essentially of "ACEMg". Specifically, treatment with the composition consisting essentially of "ACEMg" results in less than 10% of the outer hair cells in the whole cochlea were missing, and less than 15% of the outer hair cells in the trauma region were missing. It is noted that more than 15% of missing outer hair cells in the whole cochlea and more than 25% of missing outer hair cells in the trauma region is generally undesirable.

Treatment of hearing loss utilizing creatine kinase is also explored. It has been known that exposure to high intensity sound will trigger a decrease in local blood flow of the inner ear, especially at very high sound exposure levels, e.g., at 120 dB to 155 dB. At the same time, metabolic activity will remain elevated well above basal levels. At the very high sound exposure levels, a reduction in cochlear blood flow (CBF) and local vasoconstriction may subject the cochlea to severe hypoperfusion in the presence of high energy demands, leading to further increase(s) in free radical formation. Impaired energy status may then lead to activation of excitatory amino acid receptors, thereby increasing intracellular calcium and the generation of free radicals. These are all potentially damaging to the inner ear.

An initial step in the development of noise trauma may be a depletion of cellular energy stores. It is believed that agents that can buffer cellular energy stores may also be useful for treating hearing loss. An example of such an agent is creatine kinase (as previously mentioned). Creatine kinase is an enzyme involved in regulating energy metabolism in cells with intermittently high and fluctuating energy requirements, including the inner ear. The enzyme catalyzes the transfer of high-energy phosphate from phosphocreatine to Adenosine Di-Phosphate (ADP) to generate Adenosine Tri-Phosphate (ATP).

Several cytoplasmic and mitochondrial isoforms have been identified that, with the substrates creatine and phosphocreatine, constitute an intricate cellular energy buffering and transport system connecting sites of energy production to sites of energy consumption. The compounds that increase cochlear energy reserve may be protected by determining whether or not the oral administration of creatine attenuates noise-inducing hearing loss.

Referring back to FIG. 6, treatment with a composition including creatine results in a threshold shift of about 34 decibels, as averaged across all frequencies, which is less than the threshold shift of the saline control sample and composition including magnesium. However, treatment with a composition including "ACEMg" and creatine did not perform well. For instance, treatment with the composition including "ACEMg" and creatine produced a threshold shift of about 44 decibels, as averaged across all frequencies, which is almost as high as the average threshold shift of the saline control sample. As shown in FIG. 7, outer hair cell counts revealed reduced sensory cell death in both the whole cochlea and in the trauma region, compared to the saline control, with the guinea pig treated with a composition including creatine. Even further reduction in sensory cell death of the outer hair cells in the whole cochlea and in the trauma region occurs with the guinea pig treated with a composition including "ACEMg" and creatine.

Compositions including salicylate are also tested for their efficacy for treating hearing loss. Salicylate is a derivative of salicylic acid that occurs naturally in plants, and serves as a natural immune hormone and preservative. Salicylate acts as a powerful antioxidant inside the body. As shown in FIG. 6, treatment with a composition including "ACEMg" and salicylate results in a threshold shift of hearing loss, as averaged across all frequencies, that is about the same as the threshold shift of hearing loss of a composition including creatine alone. However, treatment with a composition including "ACEMg", creatine, and salicylate also did not perform as well as the composition including "ACEMg" and salicylate. For instance, treatment with the composition including "ACEMg", creatine, and salicylate produced a threshold shift of hearing loss of about 36 decibels, as averaged across all frequencies, whereas treatment of the composition including "ACEMg" and salicylate produced a threshold shift of hearing loss of about 34 decibels, as averaged across all frequencies. As shown in FIG. 7, sensory cell death of the outer hair cells in the whole cochlea and in the trauma region is slightly reduced with the guinea pig treated with the composition including "ACEMg" and salicylate compared to guinea pig treated with the composition including "ACEMg" and creatine. A further slight reduction in the sensory cell death of the outer hair cells in the whole cochlea and in the trauma region occurs with the guinea pig treated with the composition including "ACEMg", creatine, and salicylate compared to the guinea pig treated with "ACEMg" and salicylate.

In view of the results shown in FIGS. 6 and 7, the composition consisting essentially of "ACEMg" performed the best compared to all of the other compositions tested.

The inventive composition that consists essentially of vitamin A, vitamin C, vitamin E, and a vasodilator comprising magnesium, in the biologically effective amounts, provides an additive effect in treating hearing loss that is equal to or greater than a sum of the effect of the individual components. Even more, the inventive composition proves to be effective in treating hearing loss if administered as late as three days after trauma to the inner ear of the mammal. As a result, the composition of the subject disclosure provides great promise in helping to minimize hearing loss resulting from trauma to inner ears of mammals. Given the high incidence of noise-induced hearing loss in the general population worldwide, there is a great need for the inventive composition in order to minimize socioeconomic effects that persist due to noise-induced hearing loss.

Furthermore, the inventive composition that consists essentially of vitamin A, vitamin C, vitamin E, and a vasodilator comprising magnesium, in the biologically effective amounts, provides an effective treatment for treating side effects of the antibiotic-treatment, including treatment of hearing loss, kidney damage, and loss of balance. In particular, by internally administering the inventive composition in conjunction with administration of the antibiotic, alleviation of side effects of the antibiotic treatment can be accomplished that is both significant and unexpected. Even more, the composition proves to be effective in treating side effects of antibiotic treatment if administered as late as three days after the first dosage of the antibiotic is administered to the mammal. As a result, the inventive composition provide great promise in helping to minimize side effects of antibiotic treatment, especially since there are no negative side effects associated with administration of the composition and since all of the components of the composition are cost-effective, readily available, and long-proven as safe for human treatment.

Additional Examples

Gjb2 conditional knock-out (Gjb2-CKO) mice are created by breeding Gjb2$^{loxP/loxP}$ mice with Sox10-Cre PAC mice, abolishing expression of Gjb2 in supporting cells of the auditory epithelium. Mice are obtained from Sackler Faculty Medicine, Tel Aviv University and a colony is started. These mice have a congenital hearing loss with a progressive deterioration. Both genders are used. Two groups are fed a micro-nutrient enhanced chow or control chow starting at 4 weeks of age until the end of the study at 16 weeks. The micro-nutrients are beta-carotene 1.05 g/kg (converted by the body to vitamin A), vitamin C 10.29 g/kg, vitamin E 7.76 g/kg and magnesium 13.48 g/kg. The control chow is the base diet for the micro-nutrient enhanced diet. Hearing is assessed by auditory brainstem response (ABR) to pure tones at 12, 16 & 24 kHz with a 4 week measure (prior to start of chow) and at 16 weeks (prior to euthanasia). Body weights are monitored weekly. At 16 weeks of age subjects are humanely euthanized and cochleae are prepared as whole mounts and stained for actin and myosin-VIIa. Photomicrographs are taken of selected sections best showing the extent of surviving hair cells in the control and treated (ACEMg) groups. Quantitative assessment of missing outer and inner hair cells (sensory cells of the organ of Corti) is performed on the apical turn of the cochlea. Since the most apical part of the cochlea shows variability in structure across animals and this most apical portion is unlikely to contribute significantly to the functional responses (ABRs) measured at 12 kHz and higher, the more basal part of the apical turn, a region extending from 1.0 mm to 2.5 mm from the apex, is selected for detailed study and analysis. More basal regions of the cochlea, below 2.5 mm from the apex, shows little surviving organ of Corti in the majority of animals in both treatment groups leaving few animals in which surviving hair cells could be assessed.

Figure 8A:
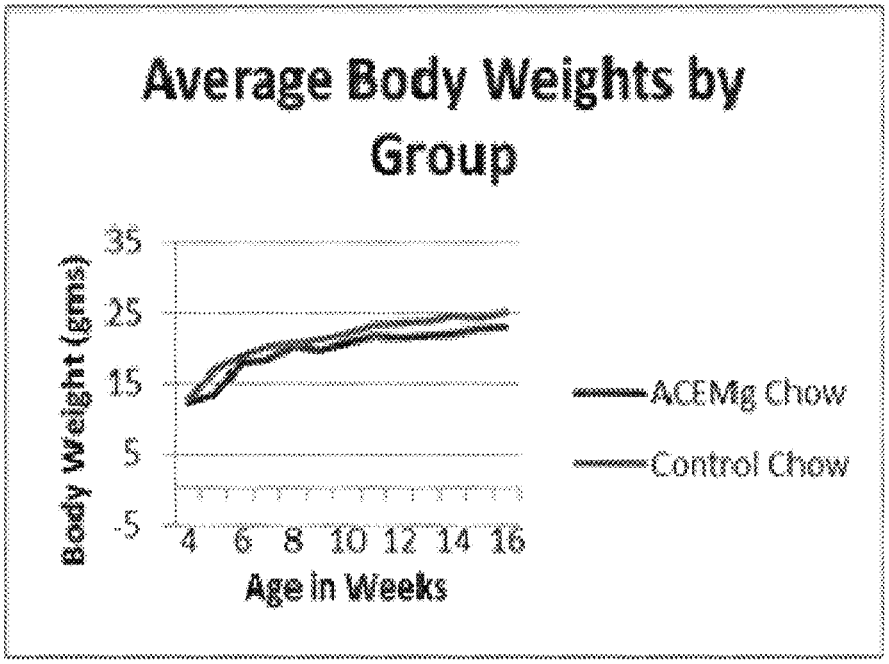
FIG. 8a is a line graph that shows the average body weight the mice in each of the experimental groups, those on the control diet and those on the ACEMg enhanced diet of the Examples.
Figure 8B:
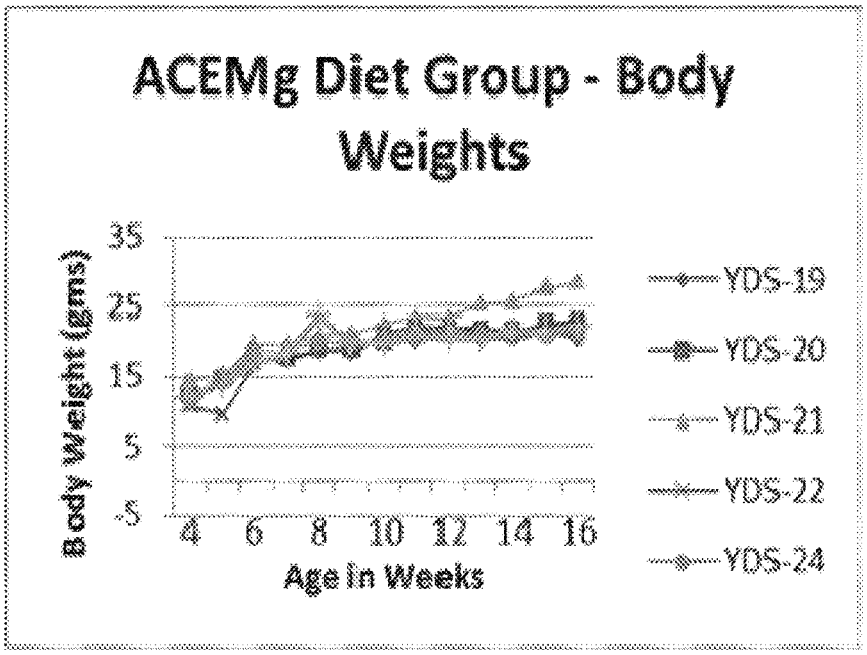
FIG. 8b is a line graph that shows the body weights of the mice on the ACEMg diet of the Examples.
Figure 8C:
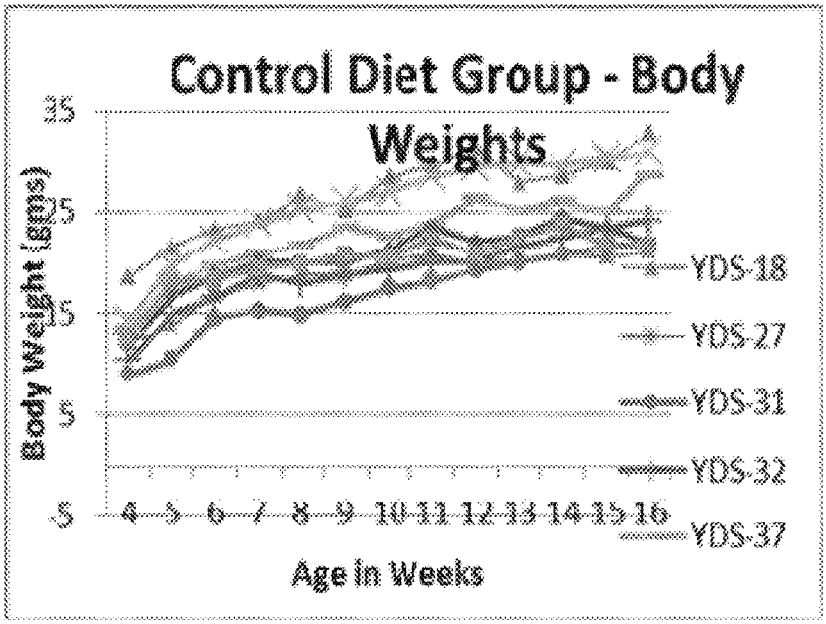
FIG. 8c is a line graph that shows the body weights of the mice on the control diet of the Examples.

FIG. 8a is a line graph that shows the average body weight for subjects in each of the experimental groups, those on the control diet and those on the ACEMg enhanced diet of the Examples. FIG. 8b is a line graph that shows the body weights of the individual animals in the ACEMg diet of the Examples. FIG. 8c is a line graph that shows the body weights of the individual animals on the control diet of the Examples. Both groups of animals gained weight normally; there was no significant difference in the mean body weight of each group.

Figure 9:
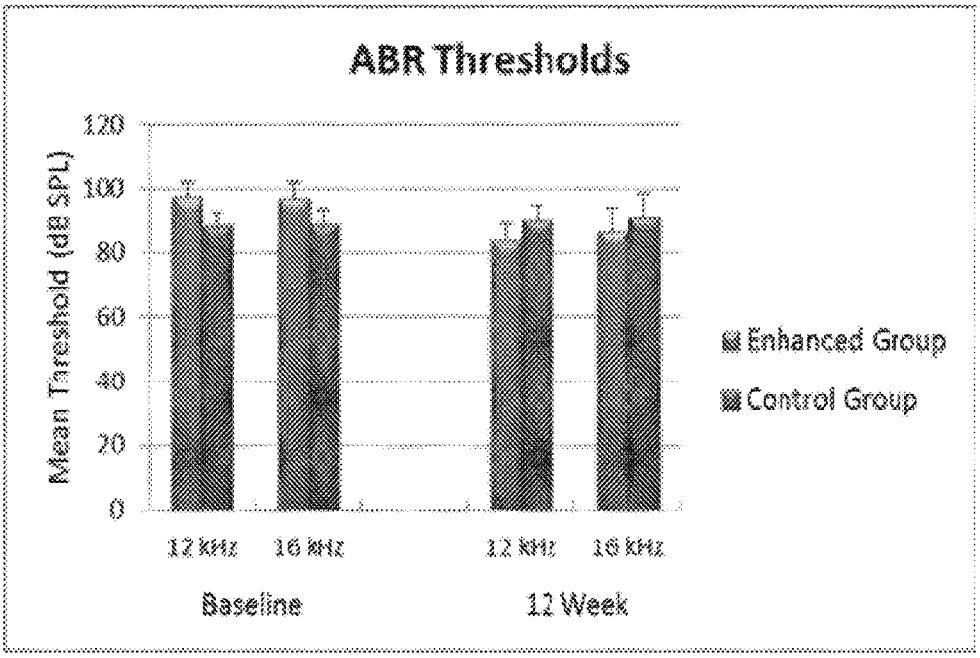
FIG. 9 is a bar graph that shows the ABR thresholds for 12 kHz and 16 kHz at the start of the study, prior to the beginning of the special diets and 12 weeks following the start of each diet, just prior to sacrifice of the animals of the Examples.

FIG. 9 is a bar graph that shows the ABR thresholds for 12 kHz and 16 kHz at the start of the study, prior to the beginning of the special diets and 12 weeks following the start of each diet, just prior to sacrifice of the animals of the Examples. ABR thresholds to 24 kHz are higher than our equipment allowed us to measure. For subjects in the ACEMg group, mean thresholds at baseline were 97.5 dB and 97.3 dB at 12 k and 16 kHz; for subjects in the control group, mean thresholds at baseline were 88.4 dB and 88.8 dB at 12 k and 16kHz. Thus at the beginning of the study the control group subjects showed a somewhat smaller hereditary hearing loss. Following 12 weeks on diet, subjects on the ACEMg diet showed somewhat lower mean thresholds than baseline: 83.8 dB and 86.5 dB for 12 k and 16 kHz respectively; while subjects on the control diet showed a slight elevation in mean threshold from baseline: 90.1 dB and 91.0 dB for 12 k and 16 kHz respectively.

Figure 10:
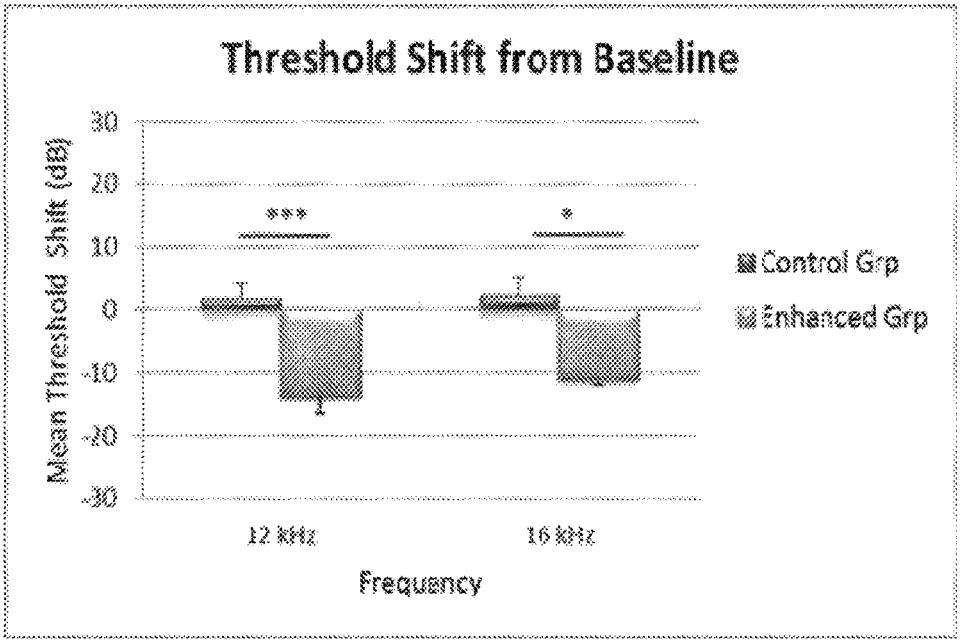
FIG. 10 is a bar graph that shows the mean change in ABR thresholds from baseline to termination (12 weeks post diet) for the control and ACEMg enhanced groups at 12 k and 16 kHz of the Examples.

FIG. 10 is a bar graph that shows the mean change in ABR thresholds from baseline to termination (12 weeks post diet) for the control and ACEMg enhanced groups at 12 k and 16 kHz. A reduction in mean threshold of greater than 10 dB was observed in the animals on the ACEMg diet, by comparison to a 1 to 2 dB elevation in threshold for the control subjects. The threshold difference in mean threshold shift from baseline was statistically significant at $p<0.001$ and 0.05 for 12 k and 16 kHz, respectively. The mean threshold shifts observed for ACEMg subjects is equivalent to a S— and 4-fold increase in hearing sensitivity.

Figure 11A:
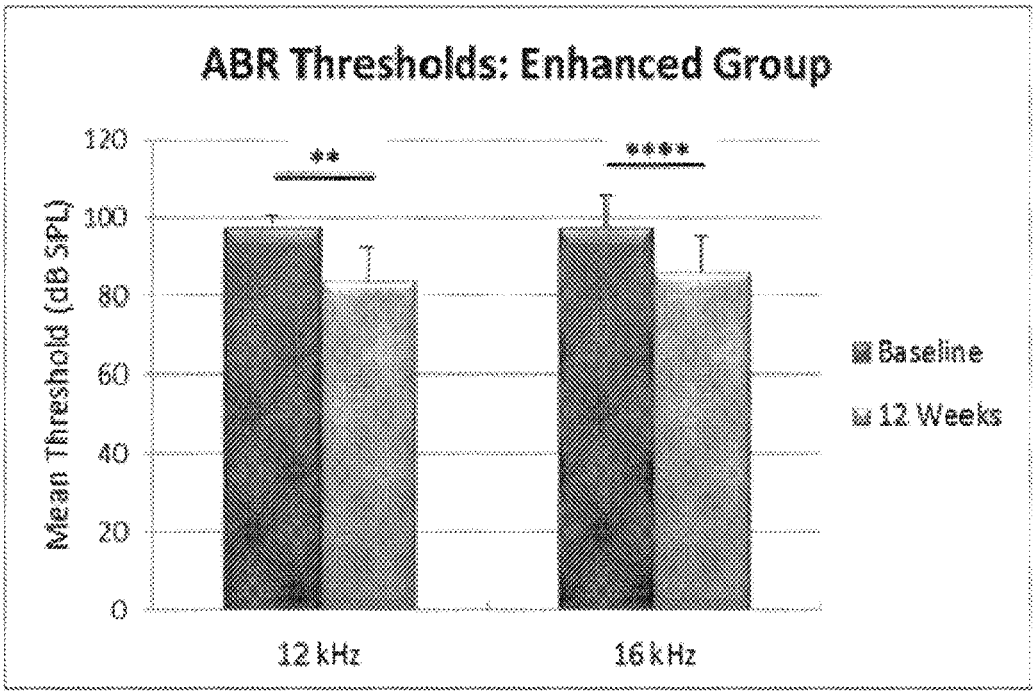
FIG. 11a is a bar graph that shows the ABR mean and SEM for thresholds at baseline and 12 weeks following the start of diet for the ACEMg group at 12 k and 16 kHz test frequencies of the Examples.
Figure 11B:
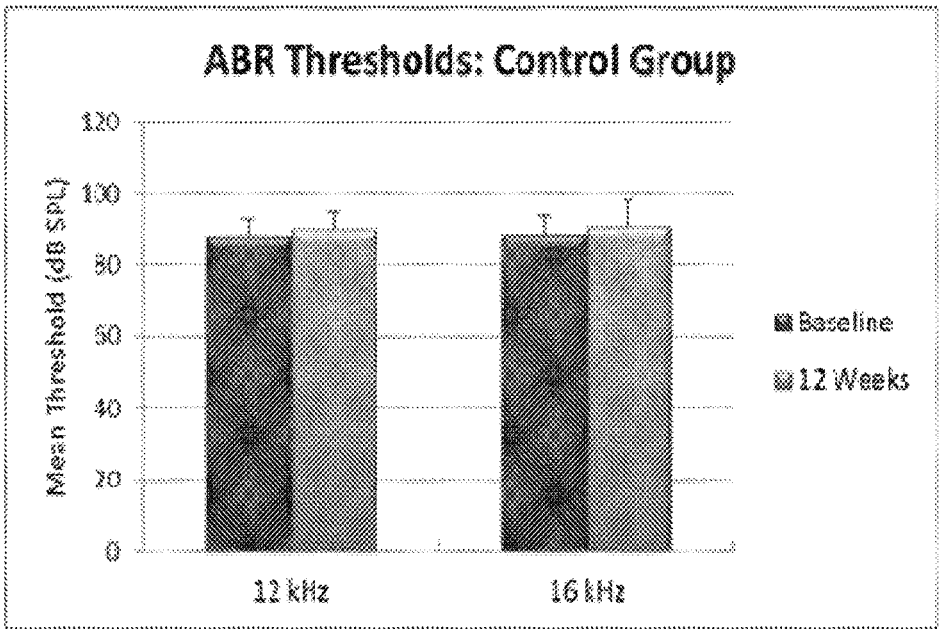
FIG. 11b is a bar graph that shows the ABR mean and SEM for thresholds at baseline and 12 weeks following the start of diet for the control group at 12 k and 16 kHz test frequencies of the Examples.

FIG. 11a is a bar graph that shows the ABR mean and SEM for thresholds at baseline and 12 weeks following the start of diet for the ACEMg group at 12 k and 16 kHz test frequencies. The observed reduction in mean thresholds at 12 k and 16 kHz were statistically significant at $p<0.01$ and 0.001, respectively. FIGS. 11b 11a is a bar graph that shows the ABR mean and SEM for thresholds at baseline and 12 weeks following the start of diet for the control group at 12 k and 16 kHz test frequencies. The mean thresholds were essentially the same at the start and at termination of the study.

Figure 12:
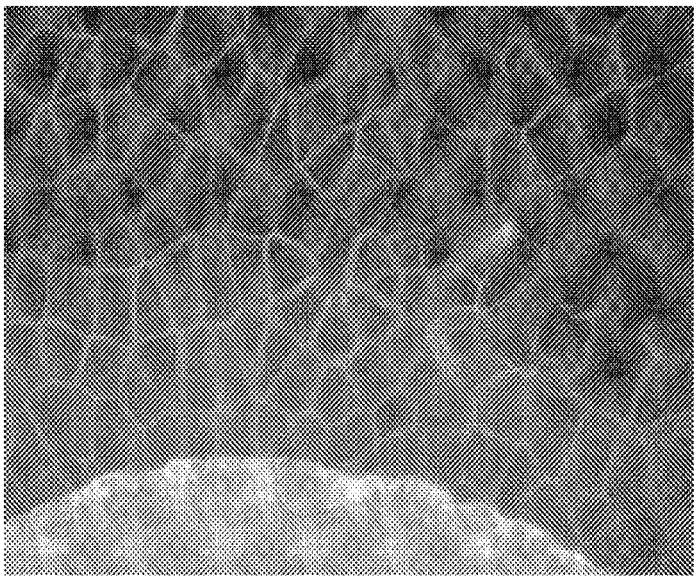
FIG. 12 is a high magnification (40×) image of the apex of the cochlea from a Cx26 mouse at 16 weeks of age (12 weeks on diet) from the control group of the Examples.

FIG. 12 is a high magnification (40×) image of the apex of the cochlea from a Cx26 mouse at 16 weeks of age (12 weeks on diet) from the control group. Only squamous epithelium is present. The organ of Corti has completely degenerated. The cochlea has a similar appearance continuing to the base. All sensory cells have degenerated.

Figure 13A:
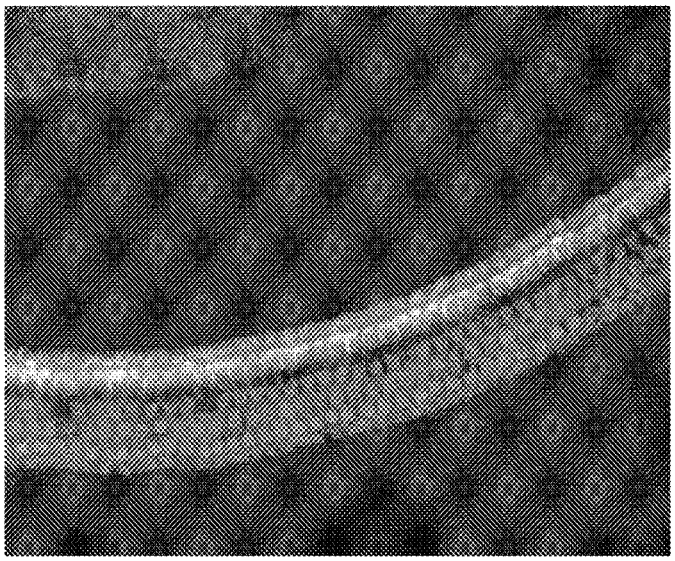
FIG. 13a is a high magnification (40×) image of the organ of Corti from a mid apical site from an animal of the Examples, wherein the organ of Corti is essentially intact, with only 2 missing outer hair cells, which is consistent with a normal mouse ear.
Figure 13B:
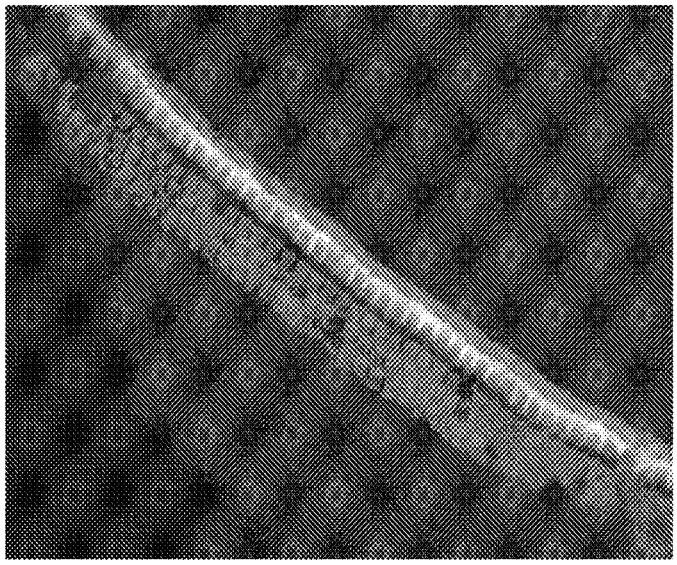
FIG. 13b is a high magnification (40×) image of the organ of Corti from an upper basal turn site from an animal of the Examples, with occasional missing outer hair cells.
Figure 13C:
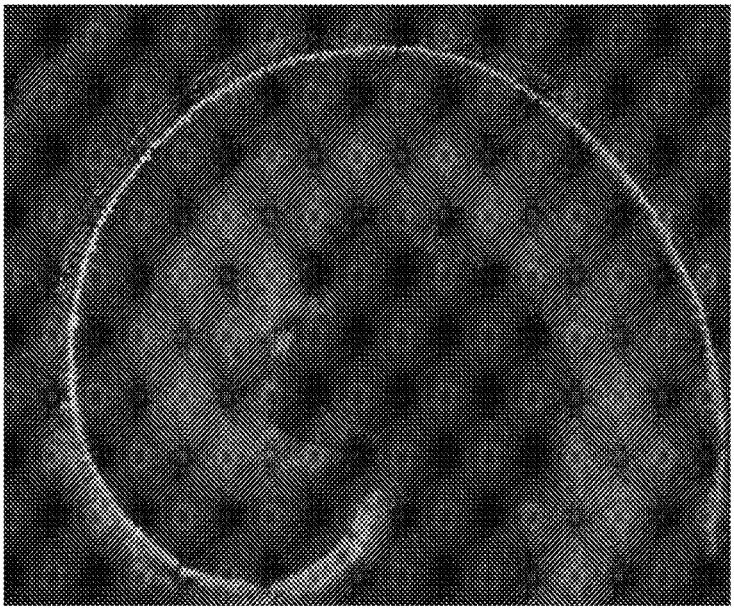
FIG. 13c is a low magnification (10×) image of surface preparation of another organ of Corti of a Cx26 mouse on ACEMg diet of the Examples.

FIG. 13a is a high magnification (40×) image of the organ of Corti from a mid apical site wherein the organ of Corti is essentially intact, with only 2 missing outer hair cells, which is consistent with a normal mouse ear. FIG. 13b is a high magnification (40×) image of the organ of Corti from an upper basal turn site, with occasional missing outer hair cells. FIG. 13c is a low magnification (10×) image of surface preparation of another organ of Corti of a Cx26 mouse on ACEMg diet. This tissue was immunostained with myo7a, selective for hair cells (green dots), and shows hair cell survival well into the basal turn of the cochlea.

Figure 14:
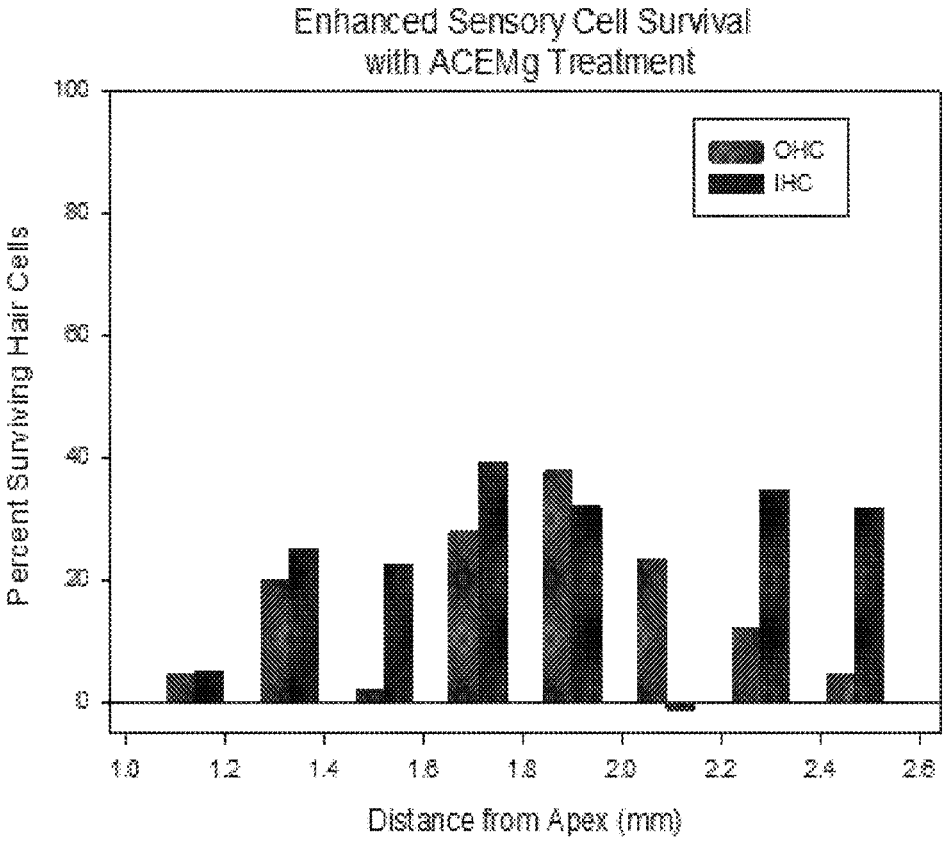
FIG. 14 is a bar graph shows the difference in surviving outer and inner hair cells (OHC and IHC, respectively) in the control and ACEMg treated CX26 mice of the Examples over a region from 1.0 mm to 2.5 mm of the organ of Corti from the apex of the cochlea.

FIG. 14 is a bar graph that shows the difference in surviving outer and inner hair cells (OHC and IHC, respectively) in the control and ACEMg treated CX26 mice over a region from 1.0 mm to 2.5 mm of the organ of Corti from the apex of the cochlea. There was a statistically significant enhancement in surviving outer hair cells ($p<0.05$) and inner hair cells ($p<0.001$) in the ACEMg treated CX26 mice.

FIG. 15-18 are tables that show the results of the statistical analysis for the mean ABR thresholds Cx26 mice in the Control Group at baseline and 12 weeks post diet for each test frequency [no significant difference], the similar analysis for the ACEMg Group [significant difference found], analysis of the difference in baseline mean thresholds for the Control and ACEMg groups at each test frequency [significant difference observed] and analysis of the mean threshold shifts observed in the ACEMg group vs the control group at each test frequency [highly significant difference observed].

FIGS. 19 and 20 are tables that show the results of statistical analysis for the surviving inner and outer hair cells in the Cx26 mice in the Control Group vs the ACEMg treated group. In each case a statistically significant difference ($p<0.0001$ and 0.5, for inner and outer hair cells, respectively) was demonstrated with greater survival in the ACEMg treated group.

The data set forth in the Figures/Tables show that the formulation of vitamins A, C, E plus magnesium offer an effective treatment for some forms of hereditary deafness, specifically inherited deafness as a result of a mutation of the GJB2 gene resulting in production of dysfunctional CX26 proteins and a dysfunctional gap junction in the supporting cells of the mammalian inner ear, e.g. connexin 26-containing cells or cells that rely on connexin 26 for metabolic function within the inner ear. In the Cx26 mouse mutant, by four weeks of age, profound hearing impairment is observed. In those then raised on a normal (control) diet, by 16 weeks of age, animals demonstrate a further increase in the hearing loss associated with a variable but generally profound degeneration of the organ of Corti. In similar animals raised for 12 weeks on a diet including supplements of vitamins A, C, E plus magnesium the data show that there is a 3 to 4 fold reduction in the hearing impairment and surviving sensory cells are found in some animals throughout greater than 50% of the cochlea from the upper one-third of the basal turn through the apex. There are occasional animals in the control group with some surviving hair cells extending into the lower apical and mid-cochlear regions. However the significant ABR threshold improvements in the ACEMg treated animals and the correlated significant greater hair cell survival in the apical region (1.0-2.5 mm) of the cochlea of the ACEMg treated group demonstrates the efficacy of this therapy for Cx26-induced hereditary hearing loss.

A Further Example

Figure 21A:
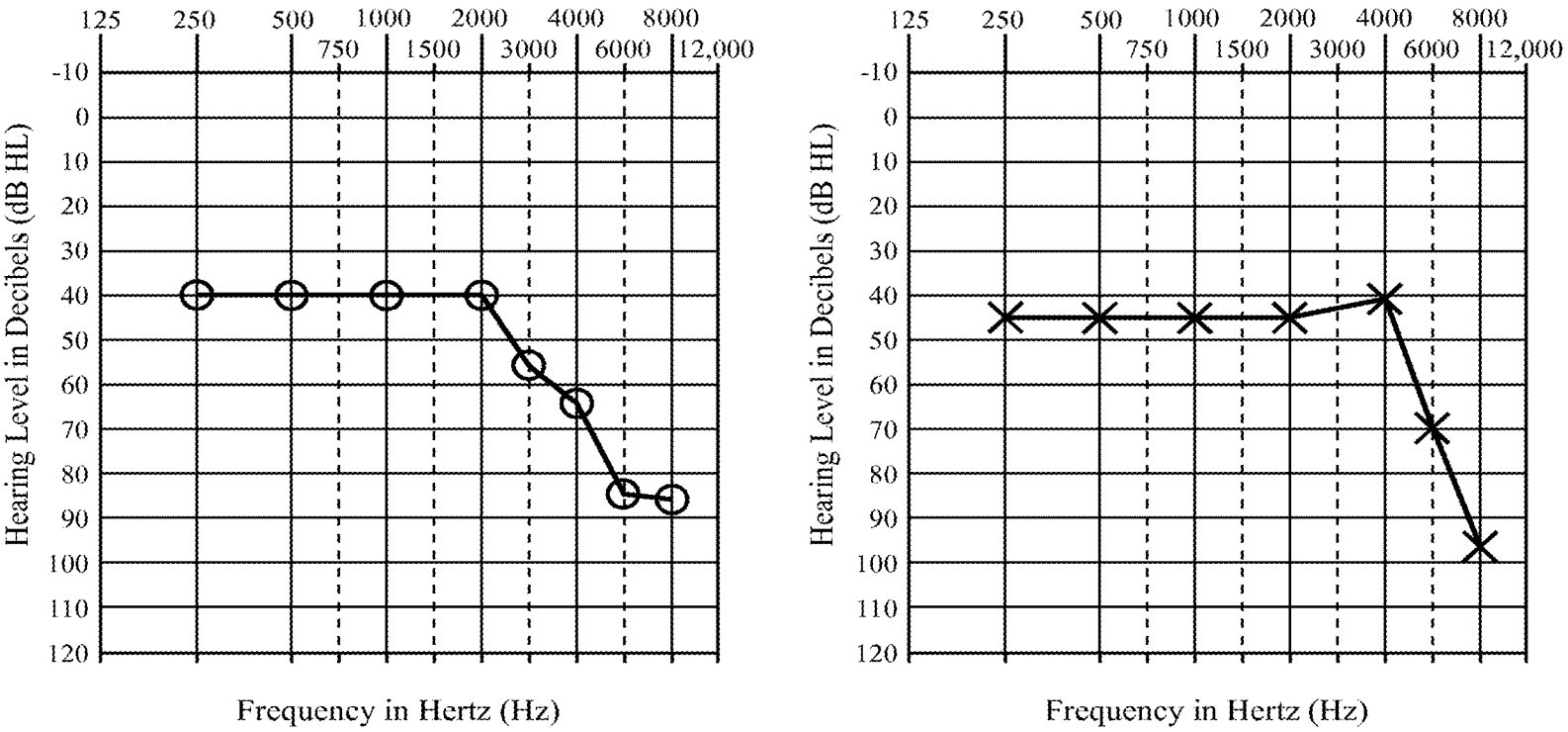
FIG. 21A is an audiogram showing speech reception thresholds of Right 45 dB and Left 45 dB of the human subject of the Examples at approximately 4.5 years of age.
Figure 21B:
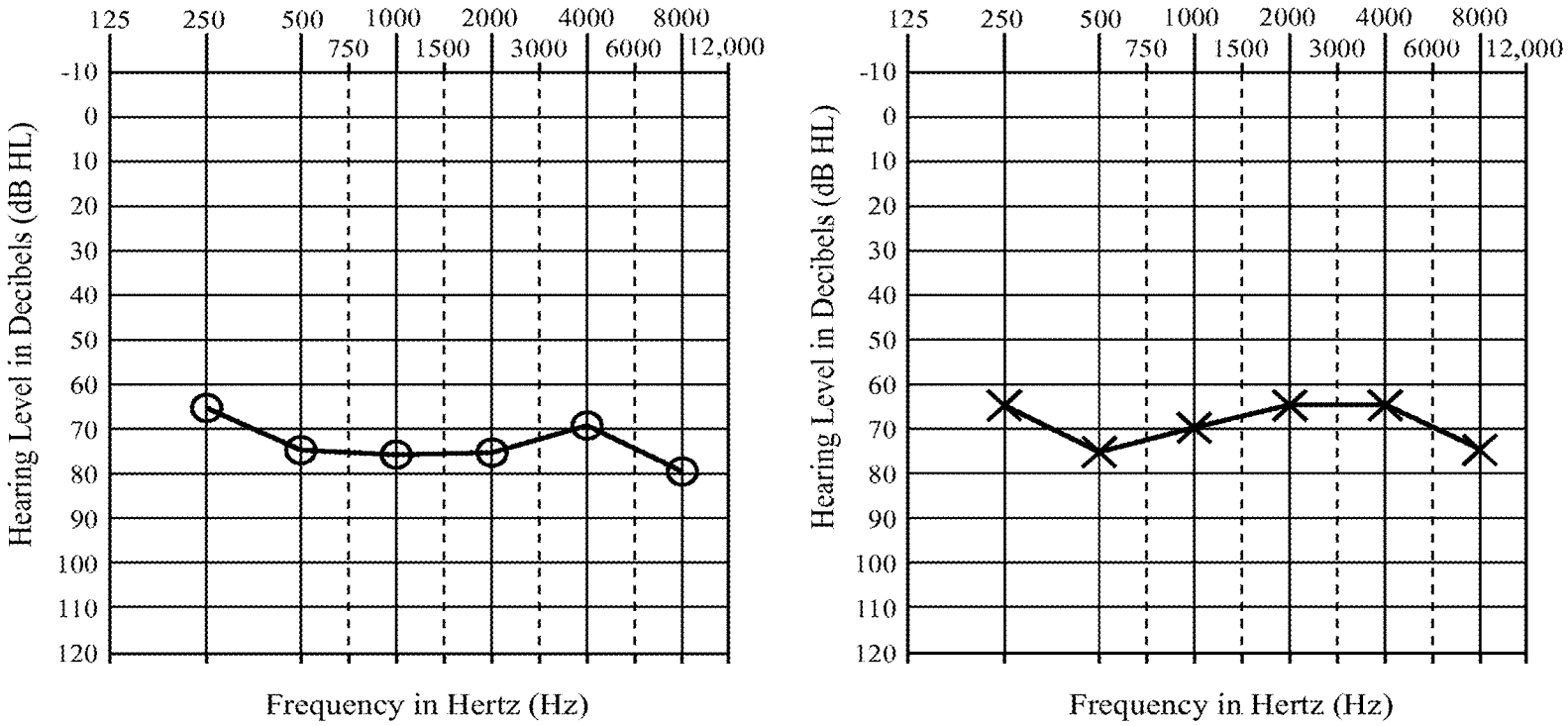
FIG. 21B is an audiogram showing speech reception thresholds of Right 75 dB and Left 70 dB of the human subject of the Examples, before treatment, at approximately 9 years of age.
Figure 21D:
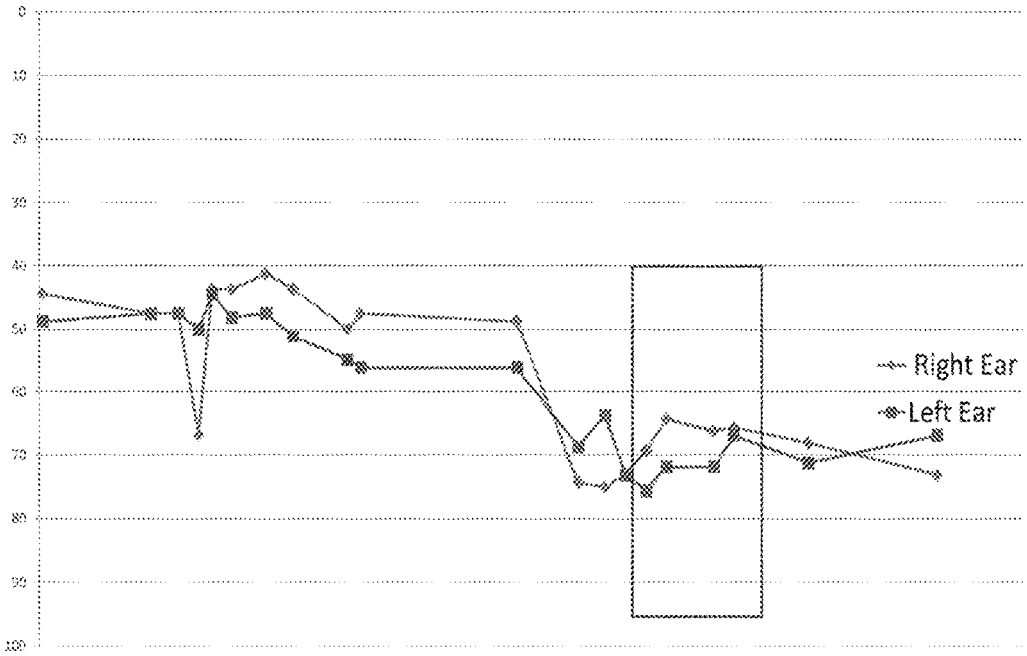
FIG. 21D is an audiometric chart setting forth hearing thresholds of right and left ears of the human subject of the Examples and includes a box that shows the interval of ACEMg administration.

An 11-year-old boy tested positive for biallelic mutations (35delG/167delT) in routine diagnostic testing with complete sequencing of the coding region of GJB2. He underwent routine otoscopic examination as well as pure tone audiometry with a diagnostic audiometer in a soundproof booth following International Standards Organization (ISO) standards. Binaural mean pure tone thresholds and speech reception thresholds are available. After 7 years with progressive hearing loss, he began a daily regimen of beta carotene (25,000 IU), ascorbic acid (10,000 IU), dl-alpha-tocopherol (400 IU) and magnesium (167 mg). Prior to commencing the nutrient regimen, his pure tone average (at 500, 1000 and 2000 Hz) dropped an average of 2.17 dB/year. Subsequent to beginning this daily supplement paradigm, audiometric evaluations have not only demonstrated no further decreases but have shown an actual improvement in hearing of 1.7 dB/year over a time period greater than one year. These changes are statistically significant ($p<0.05$). Similar changes in speech reception thresholds have also been noted. The data is summarized in FIG. 21. This data shows that a boy with Connexin 26 hearing loss and progressive hearing loss demonstrated improvement in his hearing over a nearly two year period on a nutrient regimen including otoprotective agents beta-carotene, vitamin C, vitamin E and Magnesium.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims is herein expressly contemplated. The disclosure is illustrative including words of description rather than of limitation. Many modifications and variations of the present disclosure are possible in light of the above teachings, and the disclosure may be practiced otherwise than as specifically described herein. In additional non-limiting embodiments, all values and ranges of values within any aforementioned range of numbers are hereby expressly contemplated.

What is claimed is:

1. A method of treating hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol.

2. A method as set forth in claim 1 wherein the step of internally administering the composition is further defined as orally administering the composition to the mammal.

3. A method as set forth in claim 1 wherein the step of internally administering the composition is further defined as intravenously administering the composition to the mammal.

4. A method as set forth in claim 1 further comprising the step of detecting hearing loss in a mammal.

5. A method as set forth in claim 1 wherein the step of internally administering the composition occurs prior to the step of detecting the hearing loss in the mammal.

6. A method as set forth in claim 5 wherein an average difference in threshold shift in mammals from baseline threshold sensitivity at 4, 8, and 16 kHz, as compared to an untreated control, is at least 25 decibels when the trauma results from exposure to 120 decibel SPL Octave Band Noise centered at 4 kHz for five hours.

7. A method as set forth in claim 1 wherein the composition further comprises resveratrol.

8. A method as set forth in claim 1 wherein the vitamin A is present in the composition in an amount of at least 830 IU.

9. A method as set forth in claim 1 wherein the vitamin C is present in the composition in an amount of at least 4,000 IU.

10. A method as set forth in claim 1 wherein the vitamin E is further defined as a water-soluble analogue of alpha-tocopheral.

11. A method as set forth in claim 1 wherein the vitamin E is present in the composition in an amount of at least 75 IU.

12. A method as set forth in claim 1 wherein the composition further comprises the withanolide.

13. A method as set forth in claim 1 wherein the vasodilator is present in an amount of at least 50 mg.

14. A method as set forth in claim 1 wherein the composition provides an additive effect that is equal to or greater than a sum of the effects of the individual components.

15. A method of treating hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after peroxyl radical formation.

16. A method as set forth in claim 15 wherein the formation of peroxyl radicals is further defined as oxidative DNA damage.

17. A method as set forth in claim 15 wherein the formation of peroxyl radicals is further defined as oxidative protein damage.

18. A method as set forth in claim 15 wherein the composition provides an additive effect that is equal to or greater than a sum of the effects of the individual components.

19. A method of treating hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after lipid peroxidation in the mammal.

20. A method as set forth in claim 19 wherein the composition provides an additive effect that is equal to or greater than a sum of the effects of the individual components.

21. A method of treating hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after vasoconstriction of blood vessels in an ear of the mammal.

22. A method as set forth in claim 21 wherein the composition provides an additive effect that is equal to or greater than a sum of the effects of the individual components.

23. A method of treating hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after formation of lipid peroxyl radicals within a lipophilic compartment of a mitochondrial membrane in the mammal.

24. A method as set forth in claim 23 wherein the composition provides an additive effect that is equal to or greater than a sum of the effects of the individual components.

* * * * *